(12) United States Patent
Fraley et al.

(10) Patent No.: US 6,228,871 B1
(45) Date of Patent: May 8, 2001

(54) ANGIOGENESIS INHIBITORS

(75) Inventors: Mark E. Fraley, North Wales; Randall W. Hungate, Lansdale; William F. Hoffman, Lansdale; William R. Huckle, Lansdale, all of PA (US); Richard L. Kendall, Thousand Oaks, CA (US); Kenneth A. Thomas, Jr., Chatham, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/343,652

(22) Filed: Jun. 29, 1999

Related U.S. Application Data

(60) Provisional application No. 60/092,285, filed on Jul. 10, 1995.

(51) Int. Cl.[7] .................. C07D 401/02; C07D 277/04; C07D 263/30; A61K 31/44

(52) U.S. Cl. .................. 514/340; 514/342; 514/370; 514/377; 546/269.7; 546/271.4; 548/195; 548/233

(58) Field of Search .................. 548/233, 195; 514/374, 340, 342, 370, 377; 546/269.7, 271.4

(56) References Cited

U.S. PATENT DOCUMENTS

| | | |
|---|---|---|
| 4,122,183 | 10/1978 | Neville et al. . |
| 4,946,855 | 8/1990 | Yoshinaga et al. . |
| 4,971,996 | 11/1990 | Shirashi et al. ........ 514/521 |
| 5,066,654 | 11/1991 | Taylor, Jr. et al. ........ 514/256 |
| 5,356,897 | 10/1994 | Oku et al. ........ 514/258 |
| 5,360,809 | 11/1994 | Axelsson et al. ........ 514/338 |
| 5,501,850 | 3/1996 | Stein et al. ........ 424/59 |
| 5,593,997 | 1/1997 | Dow et al. ........ 514/258 |
| 5,637,724 | 6/1997 | Desimone et al. ........ 514/367 |
| 5,665,709 | 9/1997 | Townsend et al. ........ 514/43 |

FOREIGN PATENT DOCUMENTS

| | | |
|---|---|---|
| 0 385 850 | 2/1990 | (EP) . |
| WO 92/05163 * | 4/1992 | (WO) . |
| WO 97/02266 | 6/1996 | (WO) . |
| WO 97/22596 | 6/1997 | (WO) . |
| WO 97/26258 | 6/1997 | (WO) . |

OTHER PUBLICATIONS

Shibuya, M., et al., Onogene, vol. 5, pp. 519–524, 1990.
Terman, B.I., et al., Onogene, vol. 6(6), pp. 1677–1683, 1991.
Kiyokawa, et al., Database HCAPLUS on STN AN 1995:315545, ABS. EP 594149.
Sinkula, Medicinal Chemistry, vol. 10, pp. 306–315, 1975.
Burke, Stem Cells, vol. 12, pp. 1–6, 1994.
Bellec, et al., Can. J. Chem., vol. 59(19), pp. 2826–2832, 1981.
Goldenberg, Clin. Ther., vol. 21(1), pp. 75–87, 1999.
De Kozak, et al., Ocul. Immunol. Inflamm., vol. 5(2), pp. 85–94, 1997.
Stetsenko, et al., Chemical Abstract, vol. 78(23), 1973.
Spranger, et al., Med. Klin., vol. 90(3), pp. 134–137, 1995.
Pang, et al., Oncol. Res. vol. 9(11–12), pp. 623–627, 1997.
Limb, et al., Br. J. Ophthalmol., vol. 80(2), pp. 168–173, 1996.
Windholz, et al., The Merck Index, Nineth Edition, p. 141, 1976.
Workman, et al., Cancer Biology, vol. 3, pp. 369–381, 1992.

* cited by examiner

Primary Examiner—Zinna Northington Davis
(74) Attorney, Agent, or Firm—J. Antonio Garcia-Rivas; Mark R. Daniel

(57) ABSTRACT

The present invention relates to compounds which inhibit tyrosine kinase enzymes, compositions which contain tyrosine kinase inhibiting compounds and methods of using tyrosine kinase inhibitors to treat tyrosine kinase-dependent diseases and conditions such as angiogenenesis, cancer, atherosclerosis, diabetic retinopathy or autoimmune diseases, in mammals.

27 Claims, No Drawings

ANGIOGENESIS INHIBITORS

This application claims benefit of provisional application Ser. No. 60/092,285 filed Jul. 10, 1998.

BACKGROUND OF THE INVENTION

The present invention relates to compounds which inhibit tyrosine kinase enzymes, compositions which contain tyrosine kinase inhibiting compounds and methods of using tyrosine kinase inhibitors to treat tyrosine kinase-dependent diseases/conditions such as neoangiogenesis, cancer, tumor growth, atherosclerosis, age related macular degeneration, diabetic retinopathy or inflammatory diseases, in mammals.

Tyrosine kinases are a class of enzymes that catalyze the transfer of the terminal phosphate of adenosine triphosphate to tyrosine residues in protein substrates. Tyrosine kinases are believed, by way of substrate phosphorylation, to play critical roles in signal transduction for a number of cell functions. Though the exact mechanisms of signal transduction is still unclear, tyrosine kinases have been shown to be important contributing factors in cell proliferation, carcinogenesis and cell differentiation.

Solid tumors which are treated by the present invention are cancers such as cancers of the brain, genitourinary tract, lymphatic system, stomach, larynx and lung. These include histiocytic lymphoma, lung adenocarcinoma and small cell lung cancers. Additional examples include cancers in which overexpression or activation of Raf-activating oncogenes (e.g., K-ras, erb-B) is observed. More particularly, such cancers include pancreatic and breast carcinoma.

Accordingly, inhibitors of these tyrosine kinases are useful for the prevention and treatment of proliferative diseases dependent on these enzymes.

For example, a method of treatment described herein relates to neoangiogenesis. Neoangiogenesis occurs in conjunction with tumor growth and in certain diseases of the eye. It is characterized by excessive activity of vascular endothelial growth factor.

Vascular endothelial growth factor (VEGF) binds the high affinity membrane-spanning tyrosine kinase receptors KDR and Flt-1. Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity.

Vascular growth in the retina leads to visual degeneration culminating in blindness. VEGF accounts for most of the angiogenic activity produced in or near the retina in diabetic retinopathy. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells. Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological neoangiogenesis, and these receptors are useful in the treatment of diseases in which neoangiogenesis is part of the overall pathology, e.g., inflammation, diabetic retinal vascularization, as well as various forms of cancer. The compounds of the instant invention represent novel structures for the inhibition of KDR kinase.

SUMMARY OF THE INVENTION

A compound is disclosed in accordance with formula I:

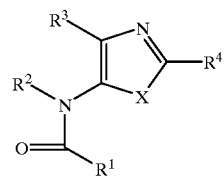

or a pharmaceutically acceptable salt, hydrate or prodrug thereof,
wherein
- X is O or S;
- $R^1$ is H, $C_{1-10}$ alkyl, $C_{3-6}$ cycloalkyl, $C_{5-10}$ aryl, halo, $CF_3$, $C_{3-10}$ heterocyclyl, or $C_{5-10}$ heteroaryl; said alkyl, alkenyl, alkynyl, aryl, heteroaryl and heterocyclyl being optionally substituted with from one to three members selected from $R^a$;
- $R^2$ is H, $C_{1-6}$ alkyl, $C_{5-10}$ aryl, $C_{5-10}$ heteroaryl, $C_{3-6}$ cycloalkyl; said alkyl, aryl, heteroaryl or cycloalkyl optionally substituted with from one to three members selected from $R^a$;
- $R^3$ is $C_{1-6}$ alkyl, $C_{5-10}$ aryl, $C_{5-10}$ heteroaryl, $C_{3-6}$ cycloalkyl; said alkyl, aryl, heteroaryl or cycloalkyl optionally substituted with from one to three members selected from $R^a$;
- $R^4$ is H, $C_{1-10}$ alkyl, $C_{3-6}$ cycloalkyl, $C_{1-6}$ alkoxy, $C_{2-10}$ kenyl, $C_{2-10}$ alkynyl, $C_{5-10}$ aryl, $C_{3-10}$ heterocyclyl, $C_{1-6}$ alkoxyNR$_7$R$_8$, $NO_2$, OH, —$NH_2$ or $C_{5-10}$ heteroaryl, said alkyl, cycloalkyl, alkenyl, alkynyl, aryl, heteroaryl and heterocyclyl being optionally substituted with from one to three members selected from $R^a$;

a is H, $C_{1-10}$ alkyl, halogen, $CF_3$, $NO_2$, NHC(O)R*, OR, —NR, $NR_7R_8$, $R_7R_8$, $C_{5-10}$ aryl, $C_{5-10}$ aralkyl, $C_{5-10}$ heteroaryl or $C_{3-10}$ heterocyclyl, said aralkyl, aryl and heteroaryl optionally substituted with 1–2 groups of $NO_2$, halo, $C_{5-10}$ aryl, $C_{1-6}$ alkoxy, $C_{1-6}$ alkyl or $CF_3$, R* is H, or $C_{1-6}$ alkyl, NHc(O)CHR($C_{5-10}$ aralkyl), the aryl ring of the aralkyl being optionally substituted with 1–3 groups of OH, $C_{1-6}$ alkyl, or halo, R is H, or $C_{1-6}$ alkyl; and $R_7$ & $R_8$ are independently H, $C_{1-10}$ alkyl, $C_{3-6}$ cycloalkyl, COR, COOR, $CO_2$, $C_{5-10}$ aryl, $C_{3-10}$ heterocyclyl, or $C_{5-10}$ heteroaryl or $NR_7R_8$ can be taken together to form a heterocyclic 5–10 membered saturated or unsaturated ring containing, in addition to the nitrogen atom, one to two additional heteroatoms selected from the group consisting of N, O and S.

Also disclosed is a pharmaceutical composition which is comprised of a compound represented by the formula I:

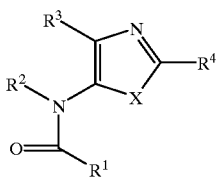

I wherein $R^1$, $R^2$, $R^3$ and $R^4$ are described as above or a pharmaceutically acceptable salt or hydrate or prodrug thereof in combination with a carrier.

Also included is a method of treating a tyrosine kinase dependent disease or condition in a mammal which comprises administering to a mammalian patient in need of such treatment a tyrosine kinase dependent disease or condition treating amount of a compound of formula I or a pharmaceutically acceptable salt, hydrate or pro-drug thereof.

Also included is a method of treating cancer in a mammalian patient in need of such treatment which is comprised of administering to said patient an anti-cancer effective amount of a compound of formula I or a pharmaceutically acceptable salt, hydrate or pro-drug thereof.

Also included in the present invention is a method of treating diseases in which neoangiogenesis is implicated, which is comprised of administering to a mammalian patient in need of such treatment a compound of formula I or a pharmaceutically acceptable salt, hydrate or pro-drug thereof in an amount which is effective for reducing neoangiogenesis.

More particularly, a method of treating ocular disease in which neoangiogenesis occurs is included herein, which is comprised of administering to a mammalian patient in need of such treatment a compound of formula I or a pharmaceutically acceptable salt hydrate or pro-drug thereof in an amount which is effective for treating said ocular disease.

More particularly, a method of treating retinal vascularization is included herein, which is comprised of administering to a mammalian patient in need of such treatment a compound of formula I or a pharmaceutically acceptable salt, hydrate or pro-drug thereof in an amount which is effective for treating retinal vascularization. Diabetic retinopathy is an example of a disease in which neoangiogenesis or retinal vascularization is part of the overall disease etiology. Also included is a method of treating age-related macular degeneration.

These and other aspects of the invention will be apparent from the teachings contained herein.

DETAILED DESCRIPTION OF THE INVENTION

The invention is described herein in detail using the terms defined below unless otherwise specified The term "alkyl" refers to a monovalent alkane (hydrocarbon) derived radical containing from 1 to 10 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopropyl, cyclobutyl, cycloheptyl, cyclopentyl and cyclohexyl.

When substituted alkyl is present, this refers to a straight, branched or cyclic alkyl group as defined above, substituted with 1–3 groups of $R^a$, described herein.

The term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted with one to three groups of $R^a$, when a substituted alkenyl group is provided.

The term "alkynyl" refers to a hydrocarbon radical straight, branched or cyclic, containing from 2 to 10 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted with 1–3 groups of $R^a$, when a substituted alkynyl group is provided.

Aryl refers to 5–10 membered aromatic rings e.g., phenyl, substituted phenyl and like groups as well bicyclic rings such as naphthyl. Aryl thus contains at least one ring having at least 5 atoms, with up to two such rings being present, containing up to 10 atoms therein. The preferred aryl groups are phenyl and naphthyl. Aryl groups may likewise be substituted with 1–3 groups of $R^a$ as defined herein. Preferred substituted aryls include phenyl and naphthyl substituted with one or two groups.

As used herein, "aralkyl" is intended to mean an aryl or heteroaryl moiety, as defined herein, attached through a $C_{1-6}$ alkyl linker, where alkyl is defined above. Examples of aralkyls include, but are not limited to, benzyl, naphthylmethyl, phenylpropyl, 2-pyridylmethyl, 2-imidazolylethyl, 2-quinolinylmethy, 2-imidazolylmethyl and the like.

The term heterocycle, heteroaryl or heterocyclic, as used herein except where noted, represents a stable 5- to 7-membered mono- or 7- to 10-membered bicyclic heterocyclic ring system, any ring of which may be saturated or unsaturated, aromatic or non-aromatic, and which consists of carbon atoms and from one to three heteroatoms selected from the group consisting of N, O and S. The nitrogen and sulfur heteroatoms may optionally be oxidized, and the nitrogen heteroatom may optionally be quaternized. Heterocycles include any bicyclic group in which any of the above-defined rings is fused to a benzene ring. The heterocyclic ring may be attached at any heteroatom or carbon atom which results in the creation of a stable structure. The heterocycle, heteroaryl or heterocyclic may be substituted with 1–3 groups of $R^a$. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thiophenyl, imidazopyridinyl, tetrazolyl, triazinyl, thienyl, benzothienyl, thiamorpholinyl sulfoxide, thiamorpholinyl sulfone, and oxadiazolyl.

The term "alkoxy" refers to a substituent with an alkyl group of the designated length in either a straight or branched configuration, and may include a double or a triple bond, which is attached via an oxygen molecule. Examples of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, vinyloxy and the like.

The term "halo" or "halogen" is intended to include the halogen atoms fluorine, chlorine, bromine and iodine.

Tyrosine kinase dependent diseases or conditions refers to hyperproliferative disorders which are initiated/maintained by aberrant expression of the activating ligands (e.g. VEGF) of the tyrosine kinases. Examples include psoriasis, cancer, immunoregulation (graft rejection), atherosclerosis, rheumatoid arthritis, angiogenesis (e.g. tumor growth, diabetic retinopathy), age related macular degeneration, etc.

One aspect of the invention is realized when X is O and all other variables are as originally described.

Another aspect of the invention is realized when X is S and all other variables are as originally described.

Still another aspect of the invention is realized when $R^3$ and $R^4$, independently, are $C_{5-10}$ aryl or $C_{5-10}$ heteroaryl optionally substituted with 1–3 groups of $R^a$.

Yet another aspect of the invention is realized when:

$R^1$ is H, $C_{1-10}$ alkyl, $C_{5-10}$ aryl, halo, $CF_3$, or $C_{5-10}$ heteroaryl; said alkyl, aryl, and heteroaryl being optionally substituted with from one to three members selected from $R^a$;

$R^2$ is H, $C_{1-6}$ alkyl or $C_{5-10}$ aryl, said alkyl or aryl optionally substituted with one to three members selected from $R^a$;

$R^3$ & $R^4$ are independently $C_{1-10}$ alkyl, $C_{5-10}$ aryl, or $C_{5-10}$ heteroaryl, said alkyl, aryl and heteroaryl being optionally substituted with from one to three members selected from $R^a$; and all other variables are as described above.

Examples of the compounds of this invention are:

2-(2-(3-hydroxy)napthyl)-4-phenyl-5-rifluoroacetamidooxazole;
2-(2-(3-hydroxy)napthyl)-4-(3-phenyl)-5-acetamidooxazole;
2-(2-(3-hydroxy)napthyl)-4-phenyl-5-acetamidooxazole;
2-(2-(3-hydroxy)napthyl)-4-(3-thiophenyl)-5-trifluoroacetamido-oxazole;
2-(2-(2-hydroxy-4-methoxy)phenyl)-4-phenyl-5-acetamidooxazole;
2-(2-(2-hydroxy-4-methyl)phenyl)-4-phenyl-5-acetamidooxazole;
2-(2-(2-hydroxy)phenyl)-4-phenyl-5-acetamidooxazole;
2-(5-isoquinolinyl)-4-phenyl-5-acetamidooxazole;
2-(2-(3-hydroxy)napthyl)-4-(3-thiophenyl)-5-acetamidooxazole;
2-(2-(3-hydroxy)napthyl)-4-phenyl-5-acetamidooxazole;
2-(3-(5-phenyl)pyridyl)-4-phenyl-5-acetamidooxazole;
2-(3-(5-(3-nitro)phenyl)pyridyl)-4-phenyl-5-acetamidooxazole;
2-(3-(5-(1-naphthyl)pyridyl)-4-phenyl-5-acetamidooxazole;
2-(3-(5-(4-methyl)phenyl)pyridyl)-4-phenyl-5-acetamidooxazole;
2-($^3$-(5-($^4$-methoxy)phenyl)pyridyl)-4-phenyl-5-acetamidooxazole;
2-(3-(5-(3-chloro)phenyl)pyridyl)-4-phenyl-5-acetamidooxazole;
2-($^3$-(5-(3-methoxy)phenyl)pyridyl)-4-phenyl-5-acetamidooxazole;
2-($^3$-(5-($^3$-fluoro)phenyl)pyridyl)-4-phenyl-5-acetamidooxazole;
2-(3-(5-(2-naphthyl)pyridyl)-4-phenyl-5-acetamidooxazole;
2-(3-(5-(2-trifluoromethyl)phenyl)pyridyl)-4-phenyl-5-acetamidooxazole;
2-(2-hydroxy)phenyl-4-phenyl-5-acetamidooxazole;
2-(2-hydroxy)phenyl-4-phenyl-5-benzamidooxazole;
2-(2-hydroxy)phenyl-4-phenyl-5-valeramidooxazole;
2-(2-hydroxy-4-phenyl)-phenyl-4-phenyl-5-acetamidooxazole;
2-(2-hydroxy-(4-(3-nitro)-phenyl))-phenyl-4-phenyl-5-acetamidooxazole;
2-(2-hydroxy-(4-(1-naphthyl))-phenyl-4-phenyl-5-acetamidooxazole;
2-(2-hydroxy-(4-(4'-methyl)-phenyl)-phenyl-4-phenyl-5-acetamidooxazole;
2-(2-hydroxy-(4-(4'-methoxy)-phenyl)-phenyl-4-phenyl-5-acetamidooxazole;
2-(2-hydroxy-(4-(3'-chloro)-phenyl)-phenyl-4-phenyl-5-acetamidooxazole;
2-(2-hydroxy-(4-(3-methoxy)-phenyl)-phenyl-4-phenyl-5-acetamidooxazole;
2-(2-hydroxy-(4-(3'-fluoro)-phenyl)-phenyl-4-phenyl-5-acetamidooxazole;
2-(2-hydroxy-(4-(2-naphthyl)-phenyl)-phenyl-4-phenyl-5-acetamidooxazole;
2-(2-hydroxy-(4-(2-trifluoromethyl)-phenyl)-phenyl-4-phenyl-5-acetamidooxazole;
2-(2-hydroxy-4-phenyl)-phenyl-4-thiophenyl-5-acetamidooxazole;
2-(2-hydroxy-(4-(3-nitro)-phenyl))-phenyl-4-thiophenyl-5-acetamidooxazole;
2-(2-hydroxy-(4-(1-naphthyl))-phenyl-4-thiophenyl-5-acetamidooxazole;
2-(2-hydroxy-(4-(4-methyl)-phenyl)-phenyl-4-thiophenyl-5-acetamidooxazole;
2-(2-hydroxy-(4-(4'-methoxy)-phenyl)-phenyl-4-thiophenyl-5-acetamidooxazole;
2-(2-hydroxy-(4-(3'-chloro)-phenyl)-phenyl-4-thiophenyl-5-acetamidooxazole;
2-(2-hydroxy-(4-(3'-methoxy)-phenyl)-phenyl-4-thiophenyl-5-acetamidooxazole;
2-(2-hydroxy-(4-(3'-fluoro)-phenyl)-phenyl-4-thiophenyl-5-acetamidooxazole;
2-(2-hydroxy-(4-(2-naphthyl)-phenyl)-phenyl-4-thiophenyl-5-acetamidooxazole;

2-(2-hydroxy-(4-(2-trifluoromethyl)-phenyl)-phenyl-4-thiophenyl-5-acetamidooxazole;
2-(2-hydroxy-4-phenyl)-phenyl-4-(3-pyridyl)-5-acetamidooxazole;
2-(2-hydroxy-(4-(3-nitro)-phenyl))-phenyl-4-(3-pyridyl)-5-acetamidooxazole;
2-(2-hydroxy-(4-(1-naphthyl))-phenyl-4-(3-pyridyl)-5-acetamidooxazole;
2-(2-hydroxy-(4-(4'-methyl)-phenyl)-phenyl-4-(3-pyridyl)-5-acetamidooxazole;
2-(2-hydroxy-(4-(4'-methoxy)-phenyl)-phenyl-4-(3-pyridyl)-5-acetamidooxazole;
2-(2-hydroxy-(4-(3'-chloro)-phenyl)-phenyl-4-(3-pyridyl)-5-acetamidooxazole;
2-(2-hydroxy-(4-(3'-methoxy)-phenyl)-phenyl-4-(3-pyridyl)-5-acetamidooxazole;
2-(2-hydroxy-(4-(3'-fluoro)-phenyl)-phenyl-4-(3-pyridyl)-5-acetamidooxazole;
2-(2-hydroxy-(4-(2-naphthyl)-phenyl)-phenyl-4-(3-pyridyl)-5-acetamidooxazole;
2-(2-hydroxy-(4-(2-trifluoromethyl)-phenyl)-phenyl-4-(3-pyridyl)-5-acetamidooxazole;
2-(2-hydroxy-4-phenyl)-phenyl-4-(3-chlorophenyl)-5-acetamidooxazole
2-(2-hydroxy-(4-(3-nitro)phenyl))-phenyl-4-(3-chlorophenyl)-5-acetamidooxazole;
2-(2-hydroxy-(4-(1-naphthyl))-phenyl-4-(3-chlorophenyl)-5-acetamidooxazole;
2-(2-hydroxy-(4-(4'-methyl)-phenyl)-phenyl-4-(3-chlorophenyl)-5-acetamidooxazole;
2-(2-hydroxy-(4-(4'-methoxy)-phenyl)-phenyl-4-(3-chlorophenyl)-5-acetamidooxazole;
2-(2-hydroxy-(4-(3'-chloro)-phenyl)-phenyl-4-(3-chlorophenyl)-5-acetamidooxazole;
2-(2-hydroxy-(4-(3'-methoxy)-phenyl)-phenyl-4-(3-chlorophenyl)-5-acetamidooxazole;
2-(2-hydroxy-(4-(3'-fluoro)-phenyl)-phenyl-4-(3-chlorophenyl)-5-acetamidooxazole;
2-(2-hydroxy-(4-(2-naphthyl)-phenyl)-phenyl-4-(3-chlorophenyl)-5-acetamidooxazole;
2-(2-hydroxy-(4-(2-trifluoromethyl)-phenyl)-phenyl-4-(3-chlorophenyl)-5-acetamidooxazole;
2-(2-hydroxy-4-phenyl)-phenyl-4-(2-chlorophenyl)-5-acetamidooxazole;
2-(2-hydroxy-(4-(3-nitro)-phenyl))-phenyl-4-(2-chlorophenyl)-5-acetamidooxazole;
2-(2-hydroxy-(4-(1-naphthyl))-phenyl-4-(2-chlorophenyl)-5-acetamidooxazole;
2-(2-hydroxy-(4-(4'-methyl)-phenyl)-phenyl-4-(2-chlorophenyl)-5-acetamidooxazole;
2-(2-hydroxy-(4-(4'-methoxy)-phenyl)-phenyl-4-(2-chorophenyl)-5-acetamidooxazole;
2-(2-hydroxy-(4-(3'-chloro)-phenyl)-phenyl-4-(2-chlorophenyl)-5-acetamidooxazole;
2-(2-hydroxy-(4-(3'-methoxy)-phenyl)-phenyl-4-(2-chlorophenyl)-5-acetamidooxazole;
2-(2-hydroxy-(4-(3'-fluoro)-phenyl)-phenyl-4-(2-chlorophenyl)-5-acetamidooxazole;
2-(2-hydroxy-(4-(2-naphthyl)-phenyl)-phenyl-4-(2-chlorophenyl)-5-acetamidooxazole;
2-(2-hydroxy-(4-(2-trifluoromethyl)-phenyl)-phenyl-4-(2-chlorophenyl)-5-acetamidooxazole;
2-(2-hydroxy-4-phenyl)-phenyl-4-(4-chlorophenyl)-5-acetamidooxazole
2-(2-hydroxy-(4-(3-nitro)-phenyl))-phenyl-4-(4-chlorophenyl)-5-acetamidooxazole;
2-(2-hydroxy-(4-(1-naphthyl))-phenyl-4-(4-chlorophenyl)-5-acetamidooxazole;
2-(2-hydroxy-(4-(4'-methyl)-phenyl)-phenyl-4-(4-chlorophenyl)-5-acetamidooxazole;
2-(2-hydroxy-(4-(4'-methoxy)-phenyl)-phenyl-4-(4-chlorophenyl)-5-acetamidooxazole;
2-(2-hydroxy-(4-(3'-chloro)-phenyl)-phenyl-4-(4-chlorophenyl)-5-acetamidooxazole;
2-(2-hydroxy-(4-(3'-methoxy)-phenyl)-phenyl-4-(4-chlorophenyl)-5-acetamidooxazole;
2-(2-hydroxy-(4-(3'-fluoro)-phenyl)-phenyl-4-(4-chlorophenyl)-5-acetamidooxazole;
2–2-hydroxy-(4-(2-naphthyl)-phenyl)-phenyl-4-(4-chlorophenyl)-5-acetamidooxazole;
2-(2-hydroxy-(4-(2-trifluoromethyl)-phenyl)-phenyl-4-(4-chlorophenyl)-5-acetamidooxazole;
2-(2-hydroxy-4-phenyl)-phenyl-4-(4-trifluoromethylphenyl)-5-acetamidooxazole;
2-(2-hydroxy-(4-(3-nitro)-phenyl))-phenyl-4-(4-trifluoromethylphenyl)-5-acetamidooxazole;
2-(2-hydroxy-(4-(1-naphthyl))-phenyl-4-(4-trifluoromethylphenyl)-5-acetamidooxazole;
2-(2-hydroxy-(4-(4'-methyl)-phenyl)-phenyl-4-(4-trifluoromethylphenyl)-5-acetamidooxazole;
2-(2-hydroxy-(4-(4'-methoxy)-phenyl)-phenyl-4-(4-trifluoromethylphenyl)-5-acetamidooxazole;
2-(2-hydroxy-(4-(3'-chloro)-phenyl)-phenyl-4-(4-trifluoromethylphenyl)-5-acetamidooxazole;
2-(2-hydroxy-(4-(3'-methoxy)-phenyl)-phenyl-4-(4-trifluoromethylphenyl)-5-acetamidooxazole;
2-(2-hydroxy-(4-(3'-fluoro)-phenyl)-phenyl-4-(4-trifluoromethylphenyl)-5-acetamidooxazole;
2-(2-hydroxy-(4-(2-naphthyl)-phenyl)-phenyl-4-(4-trifluoromethylphenyl)-5-acetamidooxazole;
2-(2-hydroxy-(4-(2-trifluoromethyl)-phenyl)-phenyl-4-(4-trifluoromethylphenyl)-5-acetamidooxazole;
2-(2-hydroxy-4-phenyl)-phenyl-4-(3-methoxyphenyl)-5-acetamidooxazole;
2-(2-hydroxy-(4-(3-nitro)-phenyl))-phenyl-4-(3-methoxyphenyl)-5-acetamidooxazole;
2-(2-hydroxy-(4-(1-naphthyl))-phenyl-4-(3-methoxyphenyl)-5-acetamidooxazole;
2-(2-hydroxy-(4-(4'-methyl)-phenyl)-phenyl-4-(3-methoxyphenyl)-5-acetamidooxazole;
2-(2-hydroxy-(4-(4'-methoxy)-phenyl)-phenyl-4-(3-methoxyphenyl)-5-acetamidooxazole;
2-(2-hydroxy-(4-(3'-chloro)-phenyl)-phenyl-4-(3-methoxyphenyl)-5-acetamidooxazole;
2-(2-hydroxy-(4-(3'-methoxy)-phenyl)-phenyl-4-(3-methoxyphenyl)-5-acetamidooxazole;
2-(2-hydroxy-(4-(3'-fluoro)-phenyl)-phenyl-4-(3-methoxyphenyl)-5-acetamidooxazole;
2-(2-hydroxy-(4-(2-naphthyl)-phenyl)-phenyl-4-(3-methoxyphenyl)-5-acetamidooxazole;
2-(2-hydroxy-(4-(2-trifluoromethyl)-phenyl)-phenyl-4-(3-methoxyphenyl)-5-acetamidooxazole;
2-(2-hydroxy-4-phenyl)-phenyl-4-(3-thiophenyl)-5-acetamidooxazole;

2-(2-hydroxy-(4-(3-nitro)-phenyl))-phenyl-4-(3-thiophenyl)-5-acetamidooxazole;

2-(2-hydroxy-(4-(1-naphthyl))-phenyl-4-(3-thiophenyl)-5-acetamidooxazole;

2-(2-hydroxy-(4-(4'-methyl)-phenyl)-phenyl-4-(3-thiophenyl)-5-acetamidooxazole;

2-(2-hydroxy-(4-(4'-methoxy)-phenyl)-phenyl-4-(3-thiophenyl)-5-acetamidooxazole;

2-(2-hydroxy-(4-(3'-chloro)-phenyl)-phenyl-4-(3-thiophenyl)-5-acetamidooxazole;

2-(2-hydroxy-(4-(3'-methoxy)-phenyl)-phenyl-4-(3-thiophenyl)-5-acetamidooxazole;

2-(2-hydroxy-(4-(3'-fluoro)-phenyl)-phenyl-4-(3-thiophenyl)-5-acetamidooxazole;

2-(2-hydroxy-(4-(2-naphthyl)-phenyl)-phenyl-4-(3-thiophenyl)-5-acetamidooxazole;

2-(2-hydroxy-(4-(2-trifluoromethyl)-phenyl)-phenyl-4-(3-thiophenyl)-5-acetamidooxazole;

2-(2-hydroxy-4-phenyl)-phenyl-4-(2-thiophenyl)-5-acetamidooxazole 2-(2-hydroxy-(4-(3-nitro)-phenyl))-phenyl-4-(2-thiophenyl)-5-acetamidooxazole;

2-(2-hydroxy-(4-(1-naphthyl))-phenyl-4-(2-thiophenyl)-5-acetamidooxazole;

2-(2-hydroxy-(4-(4'-methyl)-phenyl)-phenyl-4-(2-thiophenyl)-5-acetamidooxazole;

2-(2-hydroxy-(4-(4'-methoxy)-phenyl)-phenyl-4-(2-thiophenyl)-5-acetamidooxazole;

2-(2-hydroxy-(4-(3'-chloro)-phenyl)-phenyl-4-(2-thiophenyl)-5-acetamidooxazole;

2-(2-hydroxy-(4-(3'-methoxy)-phenyl)-phenyl-4-(2-thiophenyl)-5-acetamidooxazole;

2-(2-hydroxy-(4-(3'-fluoro)-phenyl)-phenyl-4-(2-thiophenyl)-5-acetamidooxazole;

2-(2-hydroxy-(4-(2-naphthyl)-phenyl)-phenyl-4-(2-thiophenyl)-5-acetamidooxazole;

2-(2-hydroxy-(4-(2-trifluoromethyl)-phenyl)-phenyl-4-(2-thiophenyl)-5-acetamidooxazole 2-(2-hydroxy-4-phenyl)-phenyl-4-(2,6-dichlorophenyl)-5-acetamidooxazole;

2-(2-hydroxy-(4-(3-nitro)-phenyl))-phenyl-4-(2,6-dichlorophenyl)-5-acetamidooxazole;

2-(2-hydroxy-(4-(1-naphthyl))-phenyl-4-(2,6-dichlorophenyl)-5-acetamidooxazole;

2-(2-hydroxy-(4-(4'-methyl)-phenyl)-phenyl-4-(2,6-dichlorophenyl)-5-acetamidooxazole;

2-(2-hydroxy-(4-(4'-methoxy)-phenyl)-phenyl-4-(2,6-dichlorophenyl)-5-acetamidooxazole;

2-(2-hydroxy-(4-(3'-chloro)-phenyl)-phenyl-4-(2,6-dichlorophenyl)-5-acetamidooxazole;

2-(2-hydroxy-(4-(3'-methoxy)-phenyl)-phenyl-4-(2,6-dichlorophenyl)-5-acetamidooxazole;

2-(2-hydroxy-(4-(3'-fluoro)-phenyl)-phenyl-4-(2,6-dichlorophenyl)-5-acetamidooxazole;

2-(2-hydroxy-(4-(2-naphthyl)-phenyl)-phenyl-4-(2,6-dichlorophenyl)-5-acetamidooxazole;

2-(2-hydroxy-(4-(2-trifluoromethyl)-phenyl)-phenyl-4-(2,6-dichlorophenyl)-5-acetamidooxazole;

2-(2-hydroxy-4-phenyl)-phenyl-4-phenyl-5-benzamidooxazole;

2-(2-hydroxy-(4-(3-nitro)-phenyl))-phenyl-4-phenyl-5-benzamidooxazole;

2-(2-hydroxy-(4-(1-naphthyl))-phenyl-4-phenyl-5-benzamidooxazole;

2-(2-hydroxy-(4-(4'-methyl)-phenyl)-phenyl-4-phenyl-5-benzamidooxazole;

2-(2-hydroxy-(4-(4'-methoxy)-phenyl)-phenyl-4-phenyl-5-benzamidooxazole;

2-(2-hydroxy-(4-(3'-chloro)-phenyl)-phenyl-4-phenyl-5-benzamidooxazole;

2-(2-hydroxy-(4-(3'-methoxy)-phenyl)-phenyl-4-phenyl-5-benzamidooxazole;

2-(2-hydroxy-(4-(3'-fluoro)-phenyl)-phenyl-4-phenyl-5-benzamidooxazole;

2-(2-hydroxy-(4-(2-naphthyl)-phenyl)-phenyl-4-phenyl-5-benzamidooxazole;

2-(2-hydroxy-(4-(2-trifluoromethyl)-phenyl)-phenyl-4-phenyl-5-benzamidooxazole;

2-(2-hydroxy-4-phenyl)-phenyl-4-thiophenyl-5-benzamidooxazole 2-(2-hydroxy-(4-(3-nitro)-phenyl))-phenyl-4-thiophenyl-5-benzamidooxazole;

2-(2-hydroxy-(4-(l-naphthyl))-phenyl-4-thiophenyl-5-benzamidooxazole;

2-(2-hydroxy-(4-(4'-methyl)-phenyl)-phenyl-4-thiophenyl-5-benzamidooxazole;

2-(2-hydroxy-(4-(4-methoxy)-phenyl)-phenyl-4-thiophenyl-5-benzamidooxazole;

2-(2-hydroxy-(4-(3'-chloro)-phenyl)-phenyl-4-thiophenyl-5-benzamidooxazole;

2-(2-hydroxy-(4-(3'-methoxy)-phenyl)-phenyl-4-thiophenyl-5-benzamidooxazole;

2-(2-hydroxy-(4-(3'-fluoro)-phenyl)-phenyl-4-thiophenyl-5-benzamidooxazole;

2-(2-hydroxy-(4-(2-naphthyl)-phenyl)-phenyl-4-thiophenyl-5-benzamidooxazole;

2-(2-hydroxy-(4-(2-trifluoromethyl)-phenyl)-phenyl-4-thiophenyl–5-benzamidooxazole;

2-(2-hydroxy-4-phenyl)-phenyl-4-(3-pyridyl)-5-benzamidooxazole;

2-(2-hydroxy-(4-(3-nitro)-phenyl))-phenyl-4-(3-pyridyl)-5-benzamidooxazole;

2-(2-hydroxy-(4-(1-naphthyl))-phenyl-4-(3-pyridyl)-5-benzamidooxazole;

2-(2-hydroxy-(4-(4'-methyl)-phenyl)-phenyl-4-(3-pyridyl)-[5]-benzamidooxazole;

2-(2-hydroxy-(4-(4'-methoxy)-phenyl)-phenyl-4-(3-pyridyl)-5-benzamidooxazole;

2-(2-hydroxy-(4-(3'-chloro)-phenyl)-phenyl-4-(3-pyridyl)-5-benzamidooxazole;

2-(2-hydroxy-(4-(3'-methoxy)-phenyl)-phenyl-4-(3-pyridyl)-5-benzamidooxazole;

2-(2-hydroxy-(4-(3'-fluoro)-phenyl)-phenyl-4-(3-pyridyl)-5-benzamidooxazole;

2-(2-hydroxy-(4-(2-naphthyl)-phenyl)-phenyl-4-(3-pyridyl)-5-benzamidooxazole;

2-(2-hydroxy-(4-(2-trifluoromethyl)-phenyl)-phenyl-4-(3-pyridyl)-5-benzamidooxazole;

2-(2-hydroxy-4-phenyl)-phenyl-4-(3-chlorophenyl)-5-benzamidooxazole;

2-(2-hydroxy-(4-(3-nitro)-phenyl))-phenyl-4-(3-chlorophenyl)-5-benzamidooxazole;

2-(2-hydroxy-(4-(1-naphthyl))-phenyl-4-(3-chlorophenyl)-5-benzamidooxazole;

2-(2-hydroxy-(4-(4'-methyl)-phenyl)-phenyl-4-(3-chlorophenyl)-5-benzamidooxazole;
2-(2-hydroxy-(4-(4'-methoxy)-phenyl)-phenyl-4-(3-chlorophenyl)-5-benzamidooxazole;
2-(2-hydroxy-(4-(3-chloro)-phenyl-phenyl-4-(3-chlorophenyl)-5-benzamidooxazole;
2-(2-hydroxy-(4-(3-methoxy)-phenyl)-phenyl-4-(3-chlorophenyl)-5-benzamidooxazole;
2-(2-hydroxy-(4-(3'-fluoro)-phenyl)-phenyl-4-(3-chlorophenyl)-5-benzamidooxazole;
2-(2-hydroxy-(4-(2-naphthyl)-phenyl)-phenyl-4-(3-chlorophenyl)-5-benzamidooxazole;
2-(2-hydroxy-(4-(2-trifluoromethyl)-phenyl)-phenyl-4-(3-chlorophenyl)-5-benzamidooxazole;
2-(2-hydroxy-4-phenyl)-phenyl-4-(2-chlorophenyl)-5-benzamidooxazole;
2-(2-hydroxy-(4-(3-nitro)-phenyl))-phenyl-4-(2-chlorophenyl)-5-benzamidooxazole;
2-(2-hydroxy-(4-(1-naphthyl))-phenyl-4-(2-chlorophenyl)-5-benzamidooxazole;
2-(2-hydroxy-(4-(4'-methyl)-phenyl)-phenyl-4-(2-chlorophenyl)-5-benzamidooxazole;
2-(2-hydroxy-(4-(4'-methoxy)-phenyl)-phenyl-4-(2-chlorophenyl)-5-benzamidooxazole;
2-(2-hydroxy-(4-(3'-chloro)-phenyl)-phenyl-4-(2-chlorophenyl)-5-benzamidooxazole;
2-(2-hydroxy-(4-(3-methoxy)-phenyl)-phenyl-4-(2-chlorophenyl)-5-benzamidooxazole;
2-(2-hydroxy-(4-(3'-fluoro)-phenyl)-phenyl-4-(2-chlorophenyl)-5-benzamidooxazole;
2-(2-hydroxy-(4-(2-naphthyl)-phenyl)-phenyl-4-(2-chlorophenyl)-5-benzamidooxazole;
2-(2-hydroxy-(4-(2-trifluoromethyl)-phenyl)-phenyl-4-(2-chlorophenyl)-5-benzamidooxazole;
2-(2-hydroxy-4-phenyl)-phenyl-4-(4-chlorophenyl)-5-benzamidooxazole
2-(2-hydroxy-(4-(3-nitro)-phenyl))-phenyl-4-(4-chlorophenyl)-5-benzamidooxazole;
2-(2-hydroxy-(4-(1-naphthyl))-phenyl-4-(4-chlorophenyl)-5-benzamidooxazole;
2-(2-hydroxy-(4-(4'-methyl)-phenyl)-phenyl-4-(4-chlorophenyl)-5-benzamidooxazole;
2-(2-hydroxy-(4-(4'-methoxy)-phenyl)-phenyl-4-(4-chlorophenyl)-5-benzamidooxazole;
2-(2-hydroxy-(4-(3'-chloro)-phenyl)-phenyl-4-(4-chlorophenyl)-5-benzamidooxazole;
2-(2-hydroxy-(4-(3'-methoxy)-phenyl)-phenyl-4-(4-chlorophenyl)-5-benzamidooxazole;
2-(2-hydroxy-(4-(3'-fluoro)-phenyl)-phenyl-4-(4-chlorophenyl)-5-benzamidooxazole;
2-(2-hydroxy-(4-(2-naphthyl)-phenyl)-phenyl-4-(4-chlorophenyl)-5-benzamidooxazole;
2-(2-hydroxy-(4-(2-trifluoromethyl)-phenyl)-phenyl-4-(4-chlorophenyl)-5-benzamidooxazole;
2-(2-hydroxy-4-phenyl)-phenyl-4-(4-trifluoromethylphenyl)-5-benzamidooxazole;
2-(2-hydroxy-(4-(3-nitro)-phenyl))-phenyl-4-(4-trifluoromethylphenyl)-5-benzamidooxazole;
2-(2-hydroxy-(4-(1-naphthyl))-phenyl-4-(4-trifluoromethylphenyl)-5-benzamidooxazole;
2-(2-hydroxy-(4-(4'-methyl)-phenyl)-phenyl-4-(4-trifluoromethylphenyl)-5-benzamidooxazole;
2-(2-hydroxy-(4-(4'-methoxy)-phenyl)-phenyl-4-(4-trifluoromethylphenyl)-5-benzamidooxazole;
2-(2-hydroxy-(4-(3'-chloro)-phenyl)-phenyl-4-(4-trifluoromethylphenyl)-5-benzamidooxazole;
2-(2-hydroxy-(4-(3'-methoxy)-phenyl)-phenyl-4-(4-trifluoromethylphenyl)-5-benzamidooxazole;
2-(2-hydroxy-(4-(3'-fluoro)-phenyl)-phenyl-4-(4-trifluoromethylphenyl)-5-benzamidooxazole;
2-(2-hydroxy-(4-(2-naphthyl)-phenyl)-phenyl-4-(4-trifluoromethylphenyl)-5-benzamidooxazole;
2-(2-hydroxy-(4-(2-trifluoromethyl)-phenyl)-phenyl-4-(4-trifluoromethylphenyl)-5-benzamidooxazole;
2-(2-hydroxy-4-phenyl)-phenyl-4-(3-methoxyphenyl)-5-benzamidooxazole;
2-(2-hydroxy-(4-(3-nitro)-phenyl))-phenyl-4-(3-methoxyphenyl)-5-benzamidooxazole;
2-(2-hydroxy-(4-(1-naphthyl))-phenyl-4-(3-methoxyphenyl)-5-benzamidooxazole;
2-(2-hydroxy-(4-(4'-methyl)-phenyl)-phenyl-4-(3-methoxyphenyl)-5-benzamidooxazole;
2-(2-hydroxy-(4-(4'-methoxy)-phenyl)-phenyl-4-(3-methoxyphenyl)-5-benzamidooxazole;
2-(2-hydroxy-(4-(3'-chloro)-phenyl)-phenyl-4-(3-methoxyphenyl)-5-benzamidooxazole;
2-(2-hydroxy-(4-(3'-methoxy)-phenyl)-phenyl-4-(3-methoxyphenyl)-5-benzamidooxazole;
2-(2-hydroxy-(4-(3'-fluoro)-phenyl)-phenyl-4-(3-methoxyphenyl)-5-benzamidooxazole;
2-(2-hydroxy-(4-(2-naphthyl)-phenyl)-phenyl-4-(3-methoxyphenyl)-5-benzamidooxazole;
2-(2-hydroxy-(4-(2-trifluoromethyl)-phenyl)-phenyl-4-(3-methoxyphenyl)-5-benzamidooxazole;
2-(2-hydroxy-4-phenyl)-phenyl-4-(3-thiophenyl)-5-benzamidooxazole;
2-(2-hydroxy-(4-(3-nitro)-phenyl))-phenyl-4-(3-thiophenyl)-5-benzamidooxazole;
2-(2-hydroxy-(4-(1-naphthyl))-phenyl-4-(3-thiophenyl)-5-benzamidooxazole;
2-(2-hydroxy-(4-(4'-methyl)-phenyl)-phenyl-4-(3-thiophenyl)-5-benzamidooxazole;
2-(2-hydroxy-(4-(4-methoxy)-phenyl)-phenyl-4-(3-thiophenyl)-5-benzamidooxazole;
2-(2-hydroxy-(4-(3'-chloro)-phenyl)-phenyl-4-(3-thiophenyl)-5-benzamidooxazole;
2-(2-hydroxy-(4-(3'-methoxy)-phenyl)-phenyl-4-(3-thiophenyl)-5-benzamidooxazole;
2-(2-hydroxy-(4-(3'-fluoro)-phenyl)-phenyl-4-(3-thiophenyl)-5-benzamidooxazole;
2-(2-hydroxy-(4-(2-naphthyl)-phenyl)-phenyl-4-(3-thiophenyl)-5-benzamidooxazole;
2-(2-hydroxy-(4-(2-trifluoromethyl)-phenyl)-phenyl-4-(3-thiophenyl)-5-benzamidooxazole;
2-(2-hydroxy-4-phenyl)-phenyl-4-(2-thiophenyl)-5-benzamidooxazole
2-(2-hydroxy-(4-(3-nitro)-phenyl))-phenyl-4-(2-thiophenyl)-5-benzamidooxazole;
2-(2-hydroxy-(4-(1-naphthyl))-phenyl-4-(2-thiophenyl)-5-benzamidooxazole;
2-(2-hydroxy-(4-(4'-methyl)-phenyl)-phenyl-4-(2-thiophenyl)-5-benzamidooxazole;
2-(2-hydroxy-(4-(4'-methoxy)-phenyl)-phenyl-4-(2-thiophenyl)-5-benzamidooxazole;

2-(2-hydroxy-(4-(3'-chloro)-phenyl)-phenyl-4-(2-thiophenyl)-5-benzamidooxazole;

2-(2-hydroxy-(4-(3'-methoxy)-phenyl)-phenyl-4-(2-thiophenyl)-5-benzamidooxazole;

2-(2-hydroxy-(4-(3'-fluoro)-phenyl)-phenyl-4-(2-thiophenyl)-5-benzamidooxazole;

2-(2-hydroxy-(4-(2-naphthyl)-phenyl)-phenyl-4-(2-thiophenyl)-5-benzamidooxazole;

2-(2-hydroxy-(4-(2-trifluromethyl)-phenyl-4-(2-thiophenyl)-5-benzamidooxazole;

2-(2-hydroxy-(4-(3-nitro)-phenyl))-phneyl-4-(2,6-dichlorophenyl)-5-benzamidooxazole;

2-(2-hydroxy-4-phenyl)-phenyl-4-(2,6-dichlorophenyl)-5-benzamidooxazole;

2-(2-hydroxy-(4-(1-naphthyl))-phenyl-4-(2,6-dichlorophenyl)-5-benzamidooxazole;

2-(2-hydroxy-(4-(4'-methyl)-phenyl)-phenyl-4-(2,6-dichlorophenyl)-5-benzamidooxazole;

2-(2-hydroxy-(4-(4'-methyl)-phenyl)-phenyl-4-(2,6-dichlorophenyl)-5-benzamidooxazole;

2-(2-hydroxy-(4-(3'-chloro)-phenyl)-phenyl-4-(2,6-dichlorophenyl)-5-benzamidooxazole;

2-(2-hydroxy-(4-('-methoxy)-phenyl)-phenyl-4-(2,6-dichlorophenyl)-5-benzamidooxazole;

2-(2-hydroxy-(4-(3'-fluoro)-phenyl)-phenyl-4-(2,6-dichlorophenyl)-5-benzamidooxazole;

2-(2-hydroxy-(4-(2-naphthyl)-phenyl)-phenyl-4-(2,6-dichlorophenyl)-5-benzamidooxazole;

2-(2-hydroxy-(4-(2-trifluoromethyl)-phenyl)-phenyl-4-(2,6-dichlorophenyl)-5-benzamidooxazole;

2-(2-hydroxy-4-phenyl)-phenyl-4-phenyl-5-valeramidooxazole;

2-(2-hydroxy-(4-(3-nitro)-phenyl))-phenyl-4-phenyl-5-valeramidooxazole;

2-(2-hydroxy-(4-(1-naphthyl))-phenyl-4-phenyl-5-valeramidooxazole;

2-(2-hydroxy-(4-(4'-methyl)-phenyl)-phenyl-4-phenyl-5-valeramidooxazole;

2-(2-hydroxy-(4-(4'-methoxy)-phenyl)-phenyl-4-phenyl-5-valeramidooxazole;

2-(2-hydroxy-(4-(3'-chloro)-phenyl)-phenyl-4-phenyl-5-valeramidooxazole;

2-(2-hydroxy-(4-(3'-methoxy)-phenyl)-phenyl-4-phenyl-5-valeramidooxazole;

2-(2-hydroxy-(4-(3'-fluoro)-phenyl)-phenyl-4-phenyl-5-valeramidooxazole;

2-(2-hydroxy-(4-(2-naphthyl)-phenyl)-phenyl-4-phenyl-5-valeramidooxazole;

2-(2-hydroxy-(4-(2-trifluoromethyl)-phenyl)-phenyl-4-phenyl-5-valeramidooxazole;

2-(2-hydroxy-4-phenyl)-phenyl-4-thiophenyl-5-valeramidooxazole;

2-(2-hydroxy-(4-(3-nitro)-phenyl))-phenyl-4-thiophenyl-5-valeramidooxazole;

2-(2-hydroxy-(4-(1-naphthyl))-phenyl-4-thiophenyl-5-valeramidooxazole;

2-(2-hydroxy-(4-(4'-methyl)-phenyl)-phenyl-4-thiophenyl-5-valeramidooxazole;

2-(2-hydroxy-(4-(4'-methoxy)-phenyl)-phenyl-4-thiophenyl-5-valeramidooxazole;

2-(2-hydroxy-(4-(3'-chloro)-phenyl)-phenyl-4-thiophenyl-5-valeramidooxazole;

2-(2-hydroxy-(4-(3'-methoxy)-phenyl)-phenyl-4-thiophenyl-5-valeramidooxazole;

2-(2-hydroxy-(4-(3'-fluoro)-phenyl)-phenyl-4-thiophenyl-5-valeramidooxazole;

2-(2-hydroxy-(4-(2-naphthyl)-phenyl)-phenyl-4-thiophenyl-5-valeramidooxazole;

2-(2-hydroxy-(4-(2-trifluoromethyl)-phenyl)-phenyl-4-thiophenyl-5-valeramidooxazole;

2-(2-hydroxy-4-phenyl)-phenyl-4-(3-pyridyl)-5-valeramidooxazole 2-(2-hydroxy-(4-(3-nitro)-phenyl))-phenyl-4-(3-pyridyl)-5-valeramidooxazole;

2-(2-hydroxy-(4-(1-naphthyl))-phenyl-4-(3-pyridyl)-5-valeramidooxazole;

2-(2-hydroxy-(4-(4'-methyl)-phenyl)-phenyl-4-(3-pyridyl)-5-valeramidooxazole;

2-(2-hydroxy-(4-(4'-methoxy)-phenyl)-phenyl-4-(3-pyridyl)-5-valeramidooxazole;

2-(2-hydroxy-(4-(3'-chloro)-phenyl)-phenyl-4-(3-pyridyl)-5-valeramidooxazole;

2-(2-hydroxy-(4-(3'-methoxy)-phenyl)-phenyl-4-(3-pyridyl)-5-valeramidooxazole;

2-(2-hydroxy-(4-(3'-fluoro)-phenyl)-phenyl-4-(3-pyridyl)-5-valeramidooxazole;

2-(2-hydroxy-(4-(2-naphthyl)-phenyl)-phenyl-4-(3-pyridyl)-5-valeramidooxazole;

2-(2-hydroxy-(4-(2-trifluoromethyl)-phenyl)-phenyl-4-(3-pyridyl)-5-valeramidooxazole;

2-(2-hydroxy-4-phenyl)-phenyl-4-(3-chlorophenyl)-5-valeramidooxazole;

2-(2-hydroxy-(4-(3-nitro)-phenyl))-phenyl-4-(3-chlorophenyl)-5-valeramidooxazole;

2-(2-hydroxy-(4-(1-naphthyl))-phenyl-4-(3-chlorophenyl)-5-valeramidooxazole;

2-(2-hydroxy-(4-(4'-methyl)-phenyl)-phenyl-4-(3-chlorophenyl)-5-valeramidooxazole;

2-(2-hydroxy-(4-(4-methoxy)-phenyl)-phenyl-4-(3-chlorophenyl)-5-valeramidooxazole;

2-(2-hydroxy-(4-(3'-chloro)-phenyl)-phenyl-4-(3-chlorophenyl)-5-valeramidooxazole;

2-(2-hydroxy-(4-(3'-methoxy)-phenyl)-phenyl-4-(3-chlorophenyl)-5-valeramidooxazole;

2-(2-hydroxy-(4-(3'-fluoro)-phenyl)-phenyl-4-(3-chlorophenyl)-5-valeramidooxazole;

2-(2-hydroxy-(4-(2-naphthyl)-phenyl)-phenyl-4-(3-chlorophenyl)-5-valeramidooxazole;

2-(2-hydroxy-(4-(2-trifluoromethyl)-phenyl)-phenyl-4-(3-chlorophenyl)-5-valeramidooxazole;

2-(2-hydroxy-4-phenyl)-phenyl-4-(2-chlorophenyl)-5-valeramidooxazole;

2-(2-hydroxy-(4-(3-nitro)-phenyl))-phenyl-4-(2-chlorophenyl)-5-valeramidooxazole;

2-(2-hydroxy-(4-(1-naphthyl))-phenyl-4-(2-chlorophenyl)-5-valeramidooxazole;

2-(2-hydroxy-(4-(4'-methyl)-phenyl)-phenyl-4-(2-chlorophenyl)-5-valeramidooxazole;

2-(2-hydroxy-(4-(4'-methoxy)-phenyl)-phenyl-4-(2-chlorophenyl)-5-valeramidooxazole;

2-(2-hydroxy-(4-(3'-chloro)-phenyl)-phenyl-4-(2-chlorophenyl)-5-valeramidooxazole;

2-(2-hydroxy-(4-(3'-methoxy)-phenyl)-phenyl-4-(2-chlorophenyl)-5-valeramidooxazole;

2-(2-hydroxy-(4-(3'-fluoro)-phenyl)-phenyl-4-(2-chlorophenyl)-5-valeramidooxazole;

2-(2-hydroxy-(4-(2-naphthyl)-phenyl)-phenyl-4-(2-chlorophenyl)-5-valeramidooxazole;

2-(2-hydroxy-(4-(2-trifluoromethyl)-phenyl)-phenyl-4-(2-chlorophenyl)-5-valeramidooxazole;

2-(2-hydroxy-4-phenyl)-phenyl-4-(4-chlorophenyl)-5-valeramidooxazole;

2-(2-hydroxy-(4-(3-nitro)-phenyl))-phenyl-4-(4-chlorophenyl)-5-valeramidooxazole;

2-(2-hydroxy-(4-(1-naphthyl))-phenyl-4-(4-chlorophenyl)-5-valeramidooxazole;

2-(2-hydroxy-(4-(4-methyl)-phenyl)-phenyl-4-(4-chlorophenyl)-5-valeramidooxazole;

2-(2-hydroxy-(4-(4'-methoxy)-phenyl)-phenyl-4-(4-chlorophenyl)-5-valeramidooxazole;

2-(2-hydroxy-(4-(3'-chloro)-phenyl)-phenyl-4-(4-chlorophenyl)-5-valeramidooxazole;

2-(2-hydroxy-(4-(3'-methoxy)-phenyl)-phenyl-4-(4-chlorophenyl)-5-valeramidooxazole;

2-(2-hydroxy-(4-(3'-fluoro)-phenyl)-phenyl-4-(4-chlorophenyl)-5-valeramidooxazole;

2-(2-hydroxy-(4-(2-naphthyl)-phenyl)-phenyl-4-(4-chlorophenyl)-5-valeramidooxazole;

2-(2-hydroxy-(4-(2-trifluoromethyl)-phenyl)-phenyl-4-(4-chlorophenyl)-5-valeramidooxazole;

2-(2-hydroxy-4-phenyl)-phenyl-4-(4-trifluoromethylphenyl)-5-valeramidooxazole;

2-(2-hydroxy-(4-(3-nitro)-phenyl))-phenyl-4-(4-trifluoromethylphenyl)-5-valeramidooxazole;

2-(2-hydroxy-(4-(1-naphthyl))-phenyl-4-(4-trifluoromethylphenyl)-5-valeramidooxazole;

2-(2-hydroxy-(4-(4'-methyl)-phenyl)-phenyl-4-(4-trifluoromethylphenyl)-5-valeramidooxazole;

2-(2-hydroxy-(4-(4'-methoxy)-phenyl)-phenyl-4-(4-trifluoromethylphenyl)-5-valeramidooxazole;

2-(2-hydroxy-(4-(3'-chloro)-phenyl)-phenyl-4-(4-trifluoromethylphenyl)-5-valeramidooxazole;

2-(2-hydroxy-(4-(3'-methoxy)-phenyl)-phenyl-4-(4-trifluoromethylphenyl)-5-valeramidooxazole;

2-(2-hydroxy-(4-(3'-fluoro)-phenyl)-phenyl-4-(4-trifluoromethylphenyl)-5-valeramidooxazole;

2-(2-hydroxy-(4-(2-naphthyl)-phenyl)-phenyl-4-(4-trifluoromethylphenyl)-5-valeramidooxazole;

2-(2-hydroxy-(4-(2-trifluoromethyl)-phenyl)-phenyl-4-(4-trifluoromethylphenyl)-5-valeramidooxazole;

2-(2-hydroxy-4-phenyl)-phenyl-4-(3-methoxyphenyl)-5-valeramidooxazole;

2-(2-hydroxy-(4-(3-nitro)-phenyl))-phenyl-4-(3-methoxyphenyl)-5-valeramidooxazole;

2-(2-hydroxy-(4-(1-naphthyl))-phenyl-4-(3-methoxyphenyl)-5-valeramidooxazole;

2-(2-hydroxy-(4-(4'-methyl)-phenyl)-phenyl-4-(3-methoxyphenyl)-5-valeramidooxazole;

2-(2-hydroxy-(4-(4'-methoxy)-phenyl)-phenyl-4-(3-methoxyphenyl)-5-valeramidooxazole;

2-(2-hydroxy-(4-(3'-chloro)-phenyl)-phenyl-4-(3-methoxyphenyl)-5-valeramidooxazole;

2-(2-hydroxy-(4-(3'-methoxy)-phenyl)-phenyl-4-(3-methoxyphenyl)-5-valeramidooxazole;

2-(2-hydroxy-(4-(3'-fluoro)-phenyl)-phenyl-4-(3-methoxyphenyl)-5-valeramidooxazole;

2-(2-hydroxy-(4-(2-naphthyl)-phenyl)-phenyl-4-(3-methoxyphenyl)-5-valeramidooxazole;

2-(2-hydroxy-(4-(2-trifluoromethyl)-phenyl)-phenyl-4-(3-methoxyphenyl)-5-valeramidooxazole;

2-(2-hydroxy-4-phenyl)-phenyl-4-(3-thiophenyl)-5-valeramidooxazole;

2-(2-hydroxy-(4-(3-nitro)-phenyl))-phenyl-4-(3-thiophenyl)-5-valeramidooxazole;

2-(2-hydroxy-(4-(1-naphthyl))-phenyl-4-(3-thiophenyl)-5-valeramidooxazole;

2-(2-hydroxy-(4-(4'-methyl)-phenyl)-phenyl-4-(3-thiophenyl)-5-valeramidooxazole;

2-(2-hydroxy-(4-(4'-methoxy)-phenyl)-phenyl-4-(3-thiophenyl)-5-valeramidooxazole;

2-(2-hydroxy-(4-(3¹-chloro)-phenyl)-phenyl-4-(3-thiophenyl)-5-valeramidooxazole;

2-(2-hydroxy-(4-(3'-methoxy)-phenyl)-phenyl-4-(3-thiophenyl)-5-valeramidooxazole;

2-(2-hydroxy-(4-(3'-fluoro)-phenyl)-phenyl-4-(3-thiophenyl)-5-valeramidooxazole;

2-(2-hydroxy-(4-(2-naphthyl)-phenyl)-phenyl-4-(3-thiophenyl)-5-valeramidooxazole;

2-(2-hydroxy-(4-(2-trifluoromethyl)-phenyl)-phenyl-4-(3-thiophenyl)-5-valeramidooxazole;

2-(2-hydroxy-4-phenyl)-phenyl-4-(2-thiophenyl)-5-valeramidooxazole;

2-(2-hydroxy-(4-(3-nitro)-phenyl))-phenyl-4-(2-thiophenyl)-5-valeramidooxazole;

2-(2-hydroxy-(4-(1-naphthyl))-phenyl-4-(2-thiophenyl)-5-valeramidooxazole;

2-(2-hydroxy-(4-(4'-methyl)-phenyl)-phenyl-4-(2-thiophenyl)-5-valeramidooxazole;

2-(2-hydroxy-(4-(4'-methoxy)-phenyl)-phenyl-4-(2-thiophenyl)-5-valeramidooxazole;

2-(2-hydroxy-(4-(3'-chloro)-phenyl)-phenyl-4-(2-thiophenyl)-5-valeramidooxazole;

2-(2-hydroxy-(4-(3'-methoxy)-phenyl)-phenyl-4-(2-thiophenyl)-5-valeramidooxazole;

2-(2-hydroxy-(4-(3'-fluoro)-phenyl)-phenyl-4-(2-thiophenyl)-5-valeramidooxazole;

2-(2-hydroxy-(4-(2-naphthyl)-phenyl)-phenyl-4-(2-thiophenyl)-5-valeramidooxazole;

2-(2-hydroxy-(4-(2-trifluoromethyl)-phenyl)-phenyl-4-(2-thiophenyl)-5-valeramidooxazole;

2-(2-hydroxy-4-phenyl)-phenyl-4-(2,6-dichlorophenyl)-5-valeramidooxazole;

2-(2-hydroxy-(4-(3-nitro)-phenyl))-phenyl-4-(2,6-dichlorophenyl)-5-valeramidooxazole;

2-(2-hydroxy-(4-(1-naphthyl))-phenyl-4-(2,6-dichlorophenyl)-5-valeramidooxazole;

2-(2-hydroxy-(4-(4'-methyl)-phenyl)-phenyl-4-(2,6-dichlorophenyl)-5-valeramidooxazole;

2-(2-hydroxy-(4-(4'-methoxy)-phenyl)-phenyl-4-(2,6-dichlorophenyl)-5-valeramidooxazole;

2-(2-hydroxy-(4-(3'-chloro)-phenyl)-phenyl-4-(2,6-dichlorophenyl)-5-valeramidooxazole;

2-(2-hydroxy-(4-(3'-methoxy)-phenyl)-phenyl-4-(2,6-dichlorophenyl)-5-valeramidooxazole;

2-(2-hydroxy-(4-(3'-fluoro)-phenyl)-phenyl-4-(2,6-dichlorophenyl)-5-valeramidooxazole;

2-(2-hydroxy-(4-(2-naphthyl)-phenyl)-phenyl-4-(2,6-dichlorophenyl)-5-valeramidooxazole and 2-(2-hydroxy-(4-(2-trifluoromethyl)-phenyl)-phenyl-4-(2,6-dichlorophenyl)-5-valeramidooxazole.

Schemes 1–3 for preparing the novel compounds of this invention are presented below. The examples which follow the schemes illustrate the compounds that can be synthesized by these schemes. The schemes, however, are not limited by the compounds listed nor by any particular substituents employed for illustrative purposes. The examples specifically illustrate the application of the following schemes to specific compounds.

Schemes 1 and 2 demonstrate to generalized protocols for the preparation of the required oxazoles from nitriles and diamides respectively. Scheme 3 exemplifies the synthesis of a lactam substituted compound. The reaction conditions employed are apparent from the specific examples that follow. Alternative conditions and protocols would be apparent to those skilled in the art.

SCHEME 1

Oxazoles from amide nitriles

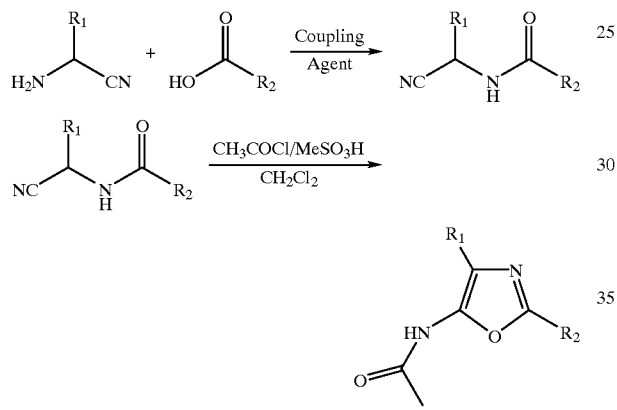

SCHEME 2

Oxazoles from diamides

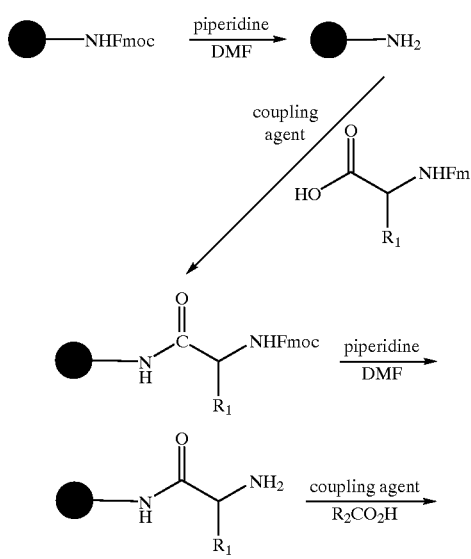

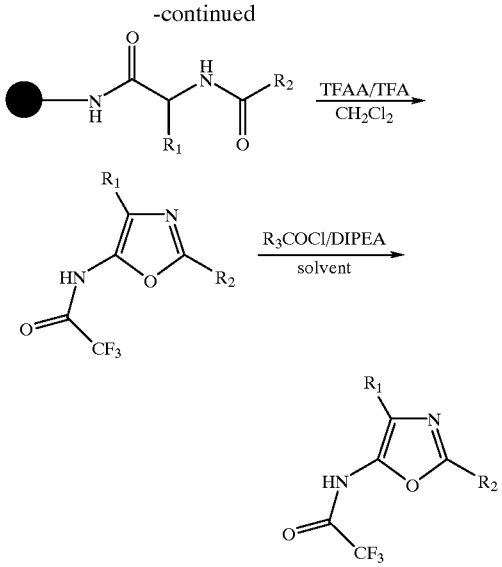

● -indicates a polymeric support

SCHEME 3

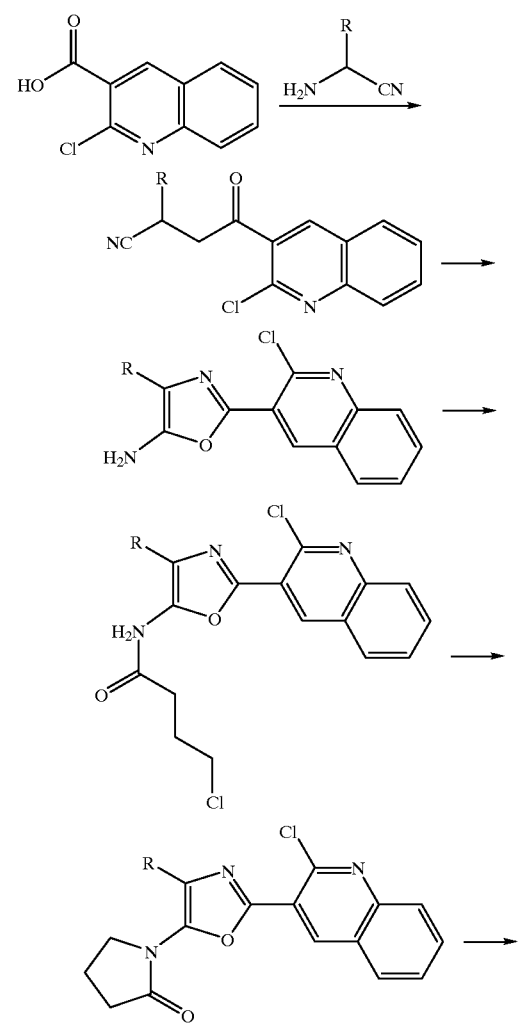

-continued

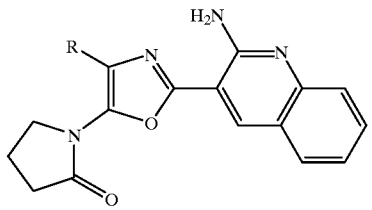

The amino thiazoles can be prepared as described in "Reactions of a α-amino- and α-acylaminothioamides with aluminum chloride. Synthesis of some imidazole and thiazole derivatives." Nyitrai, Jozsef; Lempert, Karoly. Acta Chim. (Budapest) (1972), 73(1), 43–61, or "Cyclization of ω-chloro-ω-acylamido acetophenones." Drach, B. S.; Dolgushina, I. Yu.; Sinitsa, A. D. Inst. Org. Khim., Kiev, USSR. Khim. Geterotsikl. Soedin. (1974), (7), 928–31. Conversion of the aminothiazoles to the lactam thiazoles can proceed in a similar manner described above for the corresponding amino oxazoles.

The invention described herein includes a pharmaceutical composition which is comprised of a compound of formula I or a pharmaceutically acceptable salt, hydrate or prodrug thereof in combination with a carrier. As used herein the terms "pharmaceutically acceptable salts" and "hydrates" refer to those salts and hydrated forms of the compound which would be apparent to the pharmaceutical chemist, i.e., those which favorably affect the physical or pharmacokinetic properties of the compound, such as solubility, palatability, absorption, distribution, metabolism and excretion. Other factors, more practical in nature, which are also important in the selection, are the cost of the raw materials, ease of crystallization, yield, stability, solubility, hygroscopicity and flowability of the resulting bulk drug.

When a compound of formula I is present as a salt or hydrate which is non-pharmaceutically acceptable, this can be converted to a salt or hydrate form which is pharmaceutically acceptable in accordance with the present invention.

When the compound is negatively charged, it is balanced by a counterion, e.g., an alkali metal cation such as sodium or potassium. Other suitable counterions include calcium, magnesium, zinc, ammonium, or alkylammonium cations such as tetramethylammonium, tetrabutylammonium, choline, triethylhydroammonium, meglumine, triethanolhydroammonium, etc. An appropriate number of counterions is associated with the molecule to maintain overall charge neutrality. Likewise when the compound is positively charged, e.g., protonated, an appropriate number of negatively charged counterions is present to maintain overall charge neutrality.

Pharmaceutically acceptable salts also include acid addition salts. Thus, the compound can be used in the form of salts derived from inorganic or organic acids or bases. Examples include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

The compounds of the present invention, may have asymmetric centers and occur as racemates, racemic mixtures and as individual diastereomers, or enantiomers with all isomeric forms being included in the present invention. When any variable (e.g., aryl, heteroaryl, $R^1$, etc)occurs more than one time in any constituent or in Formula I, its definition on each occcurence is independent of its definition at every other occurrence, unless otherwise stated.

The compounds of the invention can be formulated in a pharmaceutical composition by combining the compound with a pharmaceutically acceptable carrier. Examples of such compositions and carriers are set forth below.

The compounds may be employed in powder or crystalline form, in solution or in suspension. They may be administered orally, parenterally (intravenously or intramuscularly), topically, transdermally or by inhalation.

Thus, the carrier employed may be, for example, either a solid or liquid. Examples of solid carriers include lactose, terra alba, sucrose, talc, gelatin, agar, pectin, acacia, magnesium stearate, stearic acid and the like. Examples of liquid carriers include syrup, peanut oil, olive oil, water and the like. Similarly, the carrier for oral use may include time delay material well known in the art, such as glyceryl monostearate or glyceryl distearate alone or with a wax.

Topical applications may be formulated in carriers such as hydrophobic or hydrophilic bases to form ointments, creams, lotions, in aqueous, oleaginous or alcoholic liquids to form paints or in dry diluents to form powders. Such topical formulations can be used to treat ocular diseases as well as inflammatory diseases such as rheumatoid arthritis, psoriasis, contact dermatitis, delayed hypersensitivity reactions and the like.

Examples of oral solid dosage forms include tablets, capsules, troches, lozenges and the like. The size of the dosage form will vary widely, but preferably will be from about 25 mg to about 500mg. Examples of oral liquid dosage forms include solutions, suspensions, syrups, emulsions, soft gelatin capsules and the like. Examples of injectable dosage forms include sterile injectable liquids, e.g., solutions, emulsions and suspensions. Examples of injectable solids would include powders which are reconstituted, dissolved or suspended in a liquid prior to injection.

In injectable compositions, the carrier is typically comprised of sterile water, saline or another injectable liquid, e.g., peanut oil for intramuscular injections. Also, various buffering agents, preservatives and the like can be included.

For the methods of treatment disclosed herein, dosages can be varied depending upon the overall condition of the patient, the nature of the illness being treated and other factors. An example of a suitable oral dosage range is from about 0.1 to about 80 mg/kg per day, in single or divided doses. An example of a suitable parenteral dosage range is from about 0.1 to about 80 mg/kg per day, in single or divided dosages, administered by intravenous or intramuscular injection. An example of a topical dosage range is from about 0.1 mg to about 150 mg, applied externally from about one to four times a day. An example of an inhalation dosage range is from about 0.01 mg/kg to about 1 mg/kg per day.

The compounds may be administered in conventional dosages as a single agent or in combination with other therapeutically active compounds.

EXAMPLE 1

2-(2-(3-hydroxy)napthyl)-4-phenyl-5-trifluoracetamidooxazole

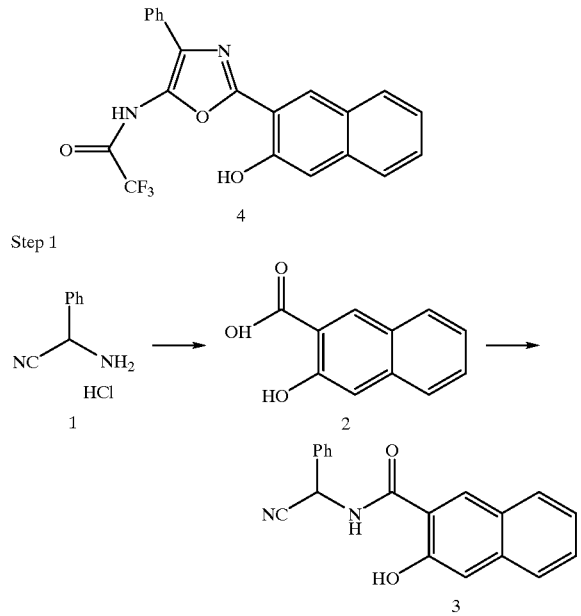

2-amino-2-phenylacetonitrile hydrochloride (1) (3.0 g, 18 mmol) and 2-hydroxy-3-napthoic acid (2) (5.1 g, 27 mmol) were dissolved in 50 mL of dimethylformamide. To this solution was added benzotriazol-1-yloxy-tripyrrolidinophosphonium hexafluorophosphate (14 g, 27mmol) and diisopropylethylamine (14 ml, 81mmol) and the reaction allowed to proceed with stirring overnight. The reaction was then concentrated and the oil taken up into ethylacetate and washed with water (3X), NaCl solution and the organics dried over sodium sulfate. Flash chromatography provided the desired product (3).

$^1$H NMR (CDCl$_3$) d 7.95 (s, 1H), 7.24–7.7 (m, 10H), 7.15 (brd, 1H), 6.38 (d, 1H).

Step 2

The amide nitrile (3) from above (1.9 g, 6.3 mmol) was treated with trifluoraceticanhydride (8.9 ml, 63 mmol) in dichloroethane containing 2% trifluoracetic. After 30 minutes the reaction was concentrated. Residue was taken up into toluene and concentrated, process was repeated to furnish slightly impure (4) which was used in the next step without further purification. $^1$H NMR (CDCl$_3$) d 8.4 (s, 1H), 7.7–7.9 (m, 4H), 7.3–7.5 (m, 6H), 3.0 (brs, 1H).

EXAMPLE 2

2-(2-(3-hydroxy)napthyl)-4-phenyl-5-acetamidooxazole

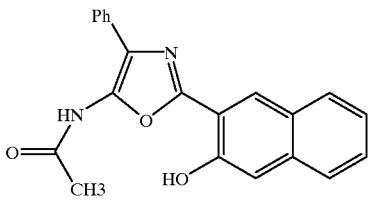

The 2-(2-(3-hydroxy)napthyl)-4-phenyl-5-trifluoracetamidooxazole (4) from above (2.5 g, 6.3 mmol) was dissolved in toluene (65 ml) and treated sequentially with diisopropylethylamine (2.2 ml, 12.6 mmol) and acetylchloride (0.90 ml, 12.6 mmol) and stirred at room temperature for 2 hours. The reaction was diluted with Ethylacetate and washed with H$_2$O (2X), NaCl and dried over Na$_2$SO$_4$. After recrystallization from MeOH/EtOAc a white solid was obtained.

$^1$H NMR (DMSO-d$_6$) d 8.5 (s, 1H), 8.2 (d, J=8.2Hz, 1H), 7.83 (m, 3H), 7.38–7.54 (m, 6H), 2.18 (brs, 3H). MS (M$^+$+1) 345.

EXAMPLE 3

2-(2-(3-hydroxy)napthyl)-4-(3-thiophenyl)-5-trifluoroacetamido-oxazole

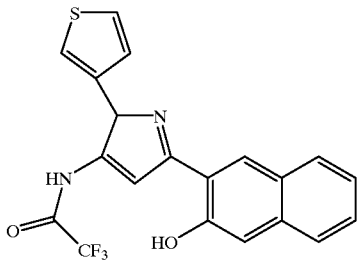

Step 1

2-amino-2-(3-thiophenyl) acetonitrile hydrochloride

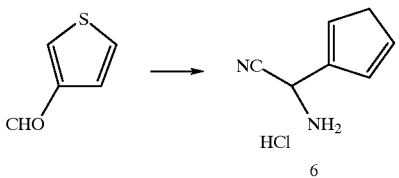

Sodium cyanide (3.77 g, 77 mmol) was dissolved in water (40 ml) followed by ammonium chloride (4.53 g, 84.7 mmol). Thiophene-3-carboxaldehyde (Aldrich, 8.66 g, 77 mmol) was dissolved in MEOH (60 ml) and added via addition funnel to the rapidly stirring solution in a steady stream. The reaction was allowed to proceed at room temperature overnight. The reaction was diluted with saturated NaHCO$_3$ and extracted with diethylether (3×100 ml). Organics were combined and washed with saturated NaCl and dried over Na$_2$SO$_4$. Organics were concentrated and the in a minimum amount of ether and filtered. The filtrate was satured with HCl gat at 0° C. The solids that formed were filtered and washed with ether to give after drying a yellow solid (6) which was used without further purification.

$^1$H NMR (DMSO-d6) d 9.8 (brs,3H), 7.91 (m, 1H), 7.70 (m, 1H), 7.43 (m, 1H), 6.04 (s, 1H).

Step 2

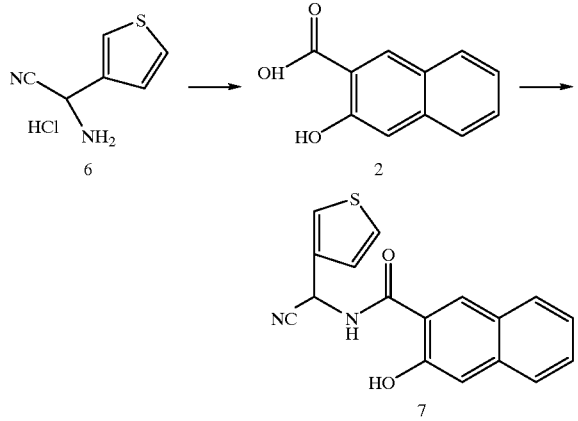

The 2-amino-2-(3-thiophenyl) acetonitrile hydrochloride (6) (1.6g, 9.17 mmol) was dissolved in DMF (90 ml) from above was treated with 2-hydroxy-3-napthoic acid (2.58 g, 13.8 mmol), benzotriazol-1-yloxy-tripyrrolidinophosphonium hexafluorophosphate (7.2 g, 13.8 mmol), 1-hydroxybenzotriazole (1.9 g, 13.8 mmol) and diisopropylethylamine (7 ml, 40 mmol) the reaction was stirred overnight at room temperature. After 18 hours the DMF was removed, the residue was taken up into EtOAc and washed successively with 1N HCl, H$_2$O, saturated NaHCO$_3$ and saturated NaCl. After purification by chromatography, product (7) was isolated.

$^1$H NMR (CDC$_{13}$) d 10.8 ( s, 1H), 7.99 (s, 1H), 7.64–7.76 (m, 3H), 7.47–7.53 (m, 2H), 7.22–7.36 (m, 4H), 7.04 (brd, J =7.7 Hz, 1H), 6.49 (d, J=8 Hz, 1H).

Step3

The amide nitrile (7) from above (280 mg, 0.93 mmol) was dissolved in CH$_2$Cl$_2$ and treated with trifluoraceticanhydride (2 ml) and trifluoracetic (0.5 ml). The reaction was allowed to proceed for 4 hours at which point it was concentrated. The solids that remained were filtered with the aid of CH$_2$Cl$_2$ and washed further with CH$_2$Cl$_2$ to give the desired product.

$^1$H NMR (CDC$_{13}$) d 10.7 (s, 1H), 8.37 (s, 1H), 7.96 (brs, 1H), 7.82 (d, J=8.4 Hz, 1H), 7.72 (d, J=8.3 Hz, 1H), 7.68 (m, 1H), 7.3–7.52 (m, 6H).

EXAMPLE 4

2-(2-(3-hydroxy)napthyl)-4-(3-thiophenyl)-5-acetamidooxazole

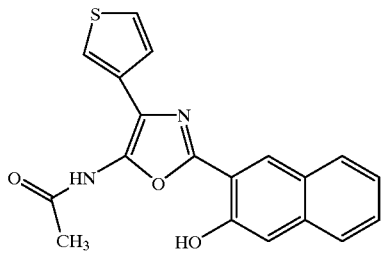

The oxazole (8) (271 mg, 0.67 mmol) from above was suspended in toluene (10 ml) and treated with acetyl chloride (0.14 ml, 2.01 mmol), and diisopropylethylamine (0.35 ml, 2.01 mmol). The reaction was allowed to stir overnight at room temperature. Reaction was diluted with ethylacetate and washed with saturated NaHCO$_3$ and saturated NaCl and dried over MgSO$_4$. The crude product was suspended in MeOH and treated with 1N NaOH (3 ml) for 15 minutes. Cloudy solution was filtered and the filtrate was neutralized with 1N HCl. The solids that formed were filtered washed with MeOH and dried under vacuum to yield the desired product (9). HRMS (M$^+$+1) found 351.0803 calculated 351.0803 for Cl$_9$H$_{15}$N2)$_3$S.

EXAMPLE 5

1-[2-(2-Amino-quinolin-3-yl-4- phenyl-oxazol-5-yl]-pyrrolidin-2-one

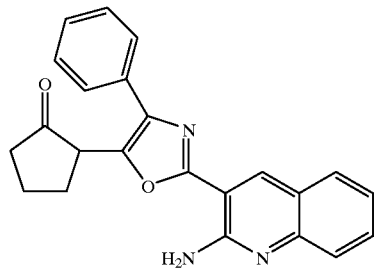

Step 1

2-chloro-quinoline-3-carboxylic acid

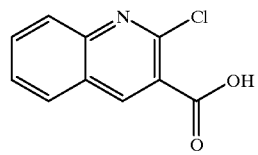

To a cold solution LDA (60 mL, 120 mmol, 2M solution) in THF (400 mL) was added 2-chloroquinoline in THF(100 mL) at such a rate to maintain temperature <70° C. The reaction was stirred for 2 hours at which point C)$_2$ was bubbled through the solution until the internal temperature reached −78° C. (−69° C. to −78° C.). The reaction was then allowed to gradually warm to room temperature overnight. After concentration to dryness, the residue taken up into diethylether and water. The layers were then separated, the aqueous phase acidified with 6N HCl and the solids collected. This material was used without further purification.

Step 2

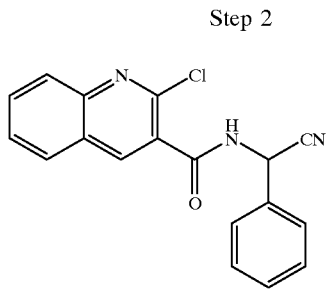

Quinoline acid from above was suspended in CH$_2$Cl$_2$ (100 mL) and cooled to -10 0C. Diphenyl phosphinic chloride was then added followed by dropwise addition of Et3N. The reaction was allowed to proceed with warming to 0° C. for one hour. The amino nitrile, suspended in CH$_2$Cl$_2$ (50 mL) containing Et$_3$N (1 equiv.), was added to the solution and reaction stirred overnight with warming to room temperature. The reaction was then concentrated to a semisolid and the residue partitional between EtOAc and water. The layers were separated and the organics washed with 0.5N HCl, water, NaHCO$_3$ (sat) water, and dried (MgSO$_4$). After the volatiles had been removed, NMR indicated that starting material remained in the residue. Therefore, the solids were stirred in NaHCO$_3$ (sat). The solids were then refiltered and taken up into EtOAc, washed with water, and dried (MgSO$_4$). The desired material was obtained by flash chromatography (10% EtOAc/CH$_2$Cl$_2$).

Step 3

N-[2-(2-Chloro-quinolin-3-yl)-4-phenyl-oxazol-5-yl]-2,2,2-trifluoro-acetamide

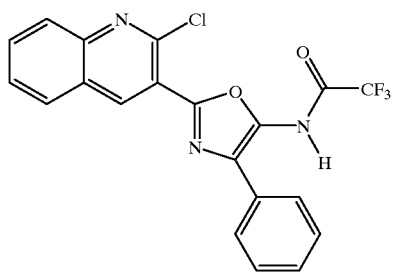

Amide nitrile from Step 2 was dissolved in a mixture of CH$_2$Cl$_2$/trifluoroacetic anhydride/trifluoroacetic acid (58140/2) and stirred at room temperature overnight. The reaction was then concentrated and the residue taken up into EtOAc. This EtOAc solution was then washed with water, aqueous NaHCO$_3$ (sat) and brine. The organics were dried with MgSO$_4$ and concentrated to afford the desired product as a solid that was used without further purification.

Step 4

4-Chloro-N-[2-(2-chloro-quinolin-3-yl)-4-phenyl-oxazol-5-yl]-butyramide

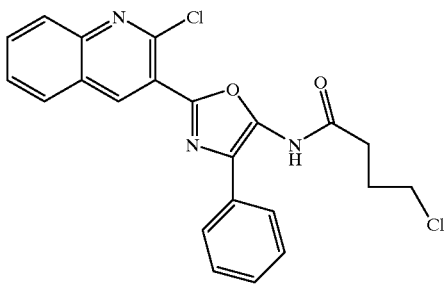

The requisite oxazole was dissolved in CH$_2$Cl$_2$ (100 mL) and treated with 4-chloro-butyl chloride and diisopropyl-ethyl amine. After 3 hours of reflux, TLC indicated that starting material still present. An additional eqiuvalent of acid chloride and base were added and the reaction refluxed for an additional two hours. The reaction was then cooled to room temperature and concentrated to a yellow gum. The residue was taken up into EtOAc and water. The layers were then separated and the organics washed with aqueous NaHCO$_3$ (sat), brine, and dried (MgSO$_4$). Flash LC (5% EtOAc/CH$_2$Cl$_2$) gave the desired product.

Step 5

1-[2-(2-chloro-quinolin-3-yl)-4-phenyl-oxazol-5-yl]-pyrolidin-2-one

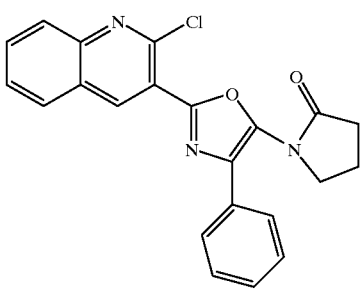

The amide was dissolved in CHCl$_3$/Et$_3$N (1:1, 30 mL) and heated to reflux overnight. The reaction was then concentrated to a yellow gum and the residue taken up into EtOAc and water. The layers were then seperated and the organics washed with brine and dried (MgSO$_4$). The material was used without further purification.

27

Step 6

1-[2-(2-Amino-quinolin-3-yl)-4-phenyl-oxazol-5-yl]-pyrrolidin-2-one

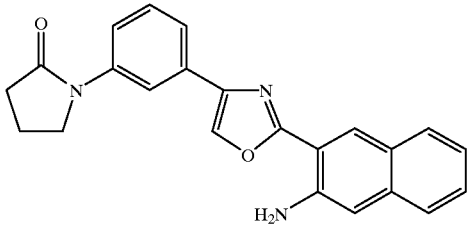

The chloroquinoline derivative from above was suspended in NH$_3$ (1) in a glass bomb. The cap was placed on the vessel and the mixture heated to 80° C. overnight. The reaction was cooled to –78° C. and contents poured into a beaker to facilitate evaporation of the NH$_3$ (1). The solid residue that remained was partitioned between EtOAc and water. The organics were washed with brine and dried (MgSO$_4$). Flash LC (20% EtOAc/CH$_2$Cl$_2$) gave the desired product plus an amount of recovered starting material.

EXAMPLE 6

1-[4-Phenyl-2-(5-thiophen-3-yl-pyridin-3-yl)-oxazol-5-yl]-pyrrolidin-2-one

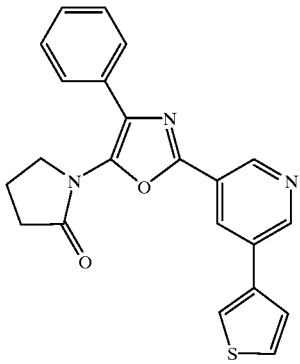

Step 1

5-Thiophen-3-yl-nicotinic acid methyl ester

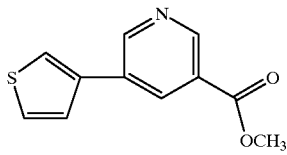

Methyl-3-bromo-nicotinate and 3-thiophene boronic acid were dissolved in degassed dioxane (25 mL). To the homogeneous solution was added Pd((Ph3)4P)). The reaction was heated to 90° C. for 18 hours and then cooled to room temperature and concentrated. The residue was taken up into EtOAc and water. The layers were then separated and the organics washed with brine and dried (MgSO$_4$). Flash LC (60% Hexanes/EtOAc) gave the desired product.

28

Step 2

5-Thiophen-3-yl-nicotinic acid

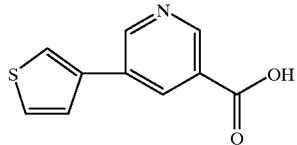

The ester from above was suspened in MeOH (20 mL), treated with 1N NaOH and stirred at room temperature for 1 hr. The reaction was then concentrated to dryness and the residue dissolved in water and neutralized with 1N HCl. The solids were filtered and dried over P$_2$O$_5$ at 50° C. for 10 hours. This material was used without further purification.

Step 3

N-(Cyano-phenyl-methyl)-5-thiophen-3-yl-nicotinamide

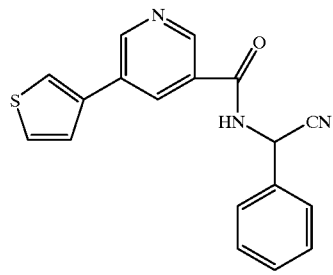

The acid from above and the benzyl amino nitrile were treated with EDC-HCl and HOAt in DMF (10 mL). The reaction was allowed to proceed overnight at room temperature. The reaction was then concentrated and the residue taken up into EtOAc and water. The layers were separated and the organics washed with aqueous NaHCO$_3$ (sat), water, and dried (MgSO$_4$). Flash LC (50% CH$_2$Cl$_2$/EtOAc) gave the desired product.

Step 4

4-Phenyl-2-(5-thiophen-3-yl-pyridin-3-yl)-oxazol-5-yl-amine

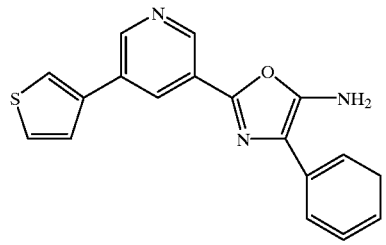

The amide nitrile (0.064 mg, 0.2 mmol) was partially dissolved in dichlorethane (5 mL). MeSO$_3$H (0.039 mL, 0.6 mmol) was then added and the reaction allowed to proceed overnight at room temperature. The reaction was diluted with CH$_2$Cl$_2$ and extracted with aqueous NaHCO$_3$ (sat), water and then dried (MgSO$_4$). The desired product was isolated by flash LC (40% EtOAc/ CH$_2$Cl$_2$) to give a pale yellow solid. The material was triturated with Et$_2$O, filtered and dried over P$_2$O$_5$.

Step 5

4-Chloro-N-[4-Phenyl-2-(5-thiophen-3-yl-pyridin-3-yl)-oxazol-5-yl]-butyramide

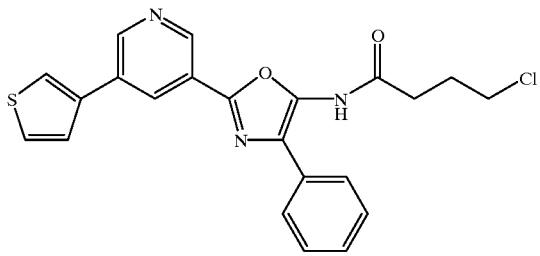

Amino oxazole (319 mg, 1.0 mmol) from above was suspended in CHCl$_3$ (75 mL) and treated with DMAP (24 mg, 0.02 mmol), Et$_3$N (0.280 mL, 2.0 mmol), and 4-chlorobutyrlchloride (0.22 mL, 2.0 mmol). The reaction was then heated to 80° C. for 6 hr wherein TLC indicated starting material still present. Two equivalents of acid chloride and Et$_3$N were then added and the reaction heated for an additional two hours. The reaction was then cooled to room temperature and concentrated to dryness. The residue was partitioned between EtOAc and NaHCO$_3$. The layers were then separated and organics washed with water and dried over MgSO$_4$. Flash LC with CH$_2$C I2 followed by 2% EtOAc/CH$_2$Cl$_2$ yield the product as a yellow gum which was used directly in the next step.

Step 6

1-[4-Phenyl-2-(5-thiophen-3-yl-pyridin-3-yl)-oxazol-5-yl]-pyrrolidin-2-one

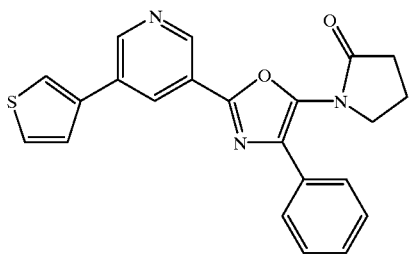

Chloro amide from above (0.38 g, 0.896 mmol) was treated with Et$_3$N (5 mL) and a small amount of CHCl$_3$ until homogeneous. The reaction was heated to 90° C. for 2 hr. The reaction was then cooled to room temperature and concentrated to dryness. The residue was partitioned between EtOAc and aqueous HCl (0.5N). The organics were washed further with water, brine, and dried (MgSO$_4$). Flash LC 5%EtOAc/CH$_2$Cl$_2$ gave an off white solid that was triturated with diethylether and dried over P$_2$O$_5$.

EXAMPLE 7

1-[2-(Hydroxy-5-methoxy-phenyl)-4-phenyl-oxazol-5-yl]-pyrrolidin-2-one

This compound was prepared in a manner analogous to that described above.

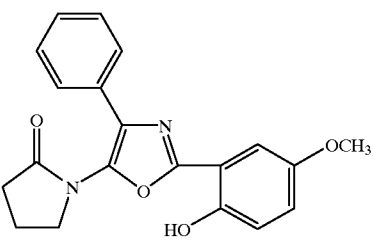

Kinase inhibition is demonstrated in accordance with the following protocol.

VEGF RECEPTOR KINASE ASSAY

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

MATERIALS

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

Lysis Buffer 50 mM Tis pH 7.4,0.5 M NaCl, 5 mM DTT, 1 mM EDTA, 0.5% triton X-100, 10 % glycerol, 10 mg/ml of each leupeptin, pepstatin and aprotinin and 1 mM phenylmethylsulfonyl fluoride (all Sigma).

Wash Buffer 50 mM Tris pH 7.4,0.5 M NaCl, 5 mM DTT, 1 mM EDTA, 0.05% triton X-100, 10 % glycerol, 10 mg/ml of each leupeptin, pepstatin and aprotinin and lmM phenylmethylsulfonyl fluoride.

Dialysis Buffer 50 mM Tris pH 7.4, 0.5 M NaCl, 5 mM DTT, 1 mM EDTA, 0.05% triton X-100, 50 % glycerol, 10 mg/ml of each leupeptin, pepstatin and aprotinin and lmM phenylmethylsuflonyl fluoride.

10 X Reaction Buffer 200 mM Tris, pH 7.4, 1.0 M NaCl, 50 mM MnCl$_2$, 10 mM DTT and 5 mg/ml bovine serum albumin (Sigma).

Enzyme Dilution Buffer 50 mM Tis, pH 7.4,0.1 M NaCl, 1 mM DTT, 10% glycerol, 100 mg/ml BSA.

10 X Substrate

750 $\mu$/ml poly (glutamic acid, tyrosine; 4:1) (Sigma).

Stop Solution

30% trichloroacetic acid, 0.2 M sodium pyrophosphate (both Fisher).

Wash Solution

15% trichloroacetic acid, 0.2 M sodium pyrophosphate.

Filter Plates

Millipore #MAFC NOB, GF/C glass fiber 96 well plate.

METHOD

A. Protein purification
1. Sf21 cells were infected with recombinant virus at a multiplicity of infection of 5 virus particles/ cell and grown at 27 ° C. for 48 hours.
2. All steps were performed at 4° C. Infected cells were harvested by centrifugation at 1000 X g and lysed at 4 ° C. for 30 minutes with 1/10 volume of lysis buffer followed by centrifugation at 100,00Xg for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF receptor kinase assay
1. Add 5 µl of inhibitor or control to the assay in 50% DMSO.
2. Add 35 µl of reaction mix containing 5 µl of 10 X reaction buffer, 5 µl 25 mM ATP/10 µCi [$^{33}$P]ATP (Amersham), and 5 µl 10 X substrate.
3. Start the reaction by the addition of 10 µl of KDR (25 nM) in enzyme dilution buffer.
4. Mix and incubate at room temperature for 15 minutes.
5. Stop by the addition of 50 µl stop solution.
6. Incubate for 15 minutes at 4° C.
7. Transfer a 90 µl aliquot to filter plate.
8. Aspirate and wash 3 times with wash solution.
9. Add 30 µl of scintillation cocktail, seal plate and count in a Wallac Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs

HUVECs frozen as primary culture isolates are obtained from Clonetics Corp. Cells are maintained in Endothelial Growth Medium (EGM; Clonetics) and are used for mitogenic assays at passages 3–7.

Culture Plates

NUNCLON 96-well polystyrene tissue culture plates (NUNC #167008).

Assay Medium

Dulbecco's modification of Eagle's medium containing 1 g/ml glucose (low-glucose DMEM; Mediatech) plus 10% (v/v) fetal bovine serum (Clonetics).

Test Compounds

Working stocks of test compounds are diluted serially in 100% dimethylsulfoxide (DMSO) to 400-fold greater than their desired final concentrations. Final dilutions to LX concentration are made directly into Assay Medium immediately prior to addition to cells.

10 X Growth factors

Solutions of human VEGF165 (500 ng/ml; R&D Systems) and bFGF (10 ng/ml; R&D Systems) are prepared in Assay Medium.

10$^3$[$^3$H]Thymidine

[Methyl-H]Thymidine (20 Ci/mmol; Dupont-NEN) is diluted to 80 µCi/ml in low-glucose DMEM.

Cell Wash Medium

Hank's balanced salt solution (Mediatech) containing 1 mg/ml bovine serum albumin (Boehringer-Mannheim).

Cell Lysis Solution

1 N NaOH, 2% (w/v) Na2CO$_3$.

Method

1. HUVEC monolayers maintained in EGM are harvested by trypsinization and plated at a density of 4000 cells per 100 ul Assay Medium per well in 96-well plates. Cells are growth-arrested for 24 hours at 37° C. in a humidified atmosphere containing 5% CO$_2$.
2. Growth-arrest medium is replaced by 100 ul Assay Medium containing either vehicle (0.25% [v/v ] DMSO) or the desired final concentration of test compound. All determinations are performed in triplicate. Cells are then incubated at 37° C./5% CO$_2$ for 2 hours to allow test compounds to enter cells.
3. After the 2-hour pretreatment period, cells are stimulated by addition of 10 ul/well of either Assay Medium, 10X VEGF solution or 10X bFGF solution. Cells are then incubated at 37° C./5% CO$_2$.
4. After 24 hours in the presence of growth factors, 10X [$^3$H]Thymidine (10 ul/well) is added.
5. Three days after addition of [$^3$H]thymidine, medium is removed by aspiration, and cells are washed twice with Cell Wash Medium (400 ul/well followed by 200 unwell). The washed, adherent cells are then solubilized by addition of Cell Lysis Solution (100 ul/well) and warming to 37° C. for 30 minutes. Cell lysates are transferred to 7-ml glass scintillation vials containing 150 ul of water. Scintillation cocktail (5 m Y hial) is added, and cell-associated radioactivity is determined by liquid scintillation spectroscopy.

Based upon the foregoing assays the compounds of formula I are inhibitors of VEGF and thus are useful for the inhibition of neoangiogenesis, such as in the treatment of occular disease, e.g., diabetic retinopathy and in the treatment of cancers, e.g., solid tumors. The instant compounds inhibit VEGF-stimulated mitogenesis of human vascular endothelial cells in culture with IC$_{50}$ values between 0.01–5.0 μM. These compounds also show selectivity over related tyrosine kinases (e.g. FGFR$_1$ and the Src family).

What is claimed is:

1. A compound in accordance with formula I:

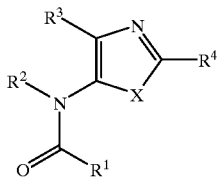

I or a pharmaceutically acceptable salt or hydrate thereof, wherein

X is O or S;

R is H, C$_{1-10}$ alkyl, C$_{3-6}$ cycloalkyl, aryl, halo, CF$_3$, C$_{3-10}$ heterocyclyl, or C$_{5-10}$ heteroaryl, said alkyl, aryl, heteroaryl and heterocyclyl being optionally substituted with one to three members selected from R$_a$;

R$^2$ is H, C$_{1-6}$ alkyl, aryl, C$_{5-10}$ heteroaryl, C$_{3-6}$ cycloalkyl, said alkyl, aryl, heteroaryl or cycloalkyl being optionally substituted with one to three members selected from R$^a$ R$^3$ is C$_{5-10}$ heteroaryl, optionally substituted with one to three members selected from R$^a$;

R$^4$ is aryl or C$_{3-10}$ heterocyclyl, said aryl and heterocyclyl is optionally substituted with one to three members selected from R$^a$;

R$^a$ is H, C$_{1-10}$ alkyl, halogen, CF$_3$, NO$_2$, NHC(O)R*, OR, NR$_7$R$_8$, aryl, C$_{5-10}$ aralkyl, C$_{5-10}$ heteroaryl or C$_{3-10}$ heterocyclyl, said aralkyl, aryl and heteroaryl optionally substituted with one or two groups selected from NO$_2$, halo, aryl, C$_{1-6}$-alkoxy, C$_{1-6}$ alkyl, and CF$_3$;

R* is H, or C$_{1-6}$ alkyl, NHC(O)CHR(C$_{5-10}$ aralkyl), wherein the aryl ring of the aralkyl may be optionally substituted with one, two or three groups selected from OH, C$_{1-6}$ alkyl, and halo;

R is H or C$_{1-6}$ alkyl; and

R$_7$ and R$_8$ are independently selected from:
H, C$_{1-10}$ alkyl, C$_{3-6}$ cycloalkyl, COR, COOR, aryl, C$_{3-10}$ heterocyclyl, or C$_{5-10}$ heteroaryl or NR$_7$R$_8$ can be taken together to form a heterocyclic 5–10 membered saturated or unsaturated ring containing, in addition to the nitrogen atom, one to two additional heteroatoms selected from the group consisting of N, O and S.

2. A compound in accordance with claim 1 wherein:

R$^1$ is H, C$_{1-10}$ alkyl, aryl, halo, CF$_3$, or C$_{5-10}$ heteroaryl, said alkyl, aryl, and heteroaryl being optionally substituted with one to three members selected from R$^a$; and R$^2$ is H, C$_{1-6}$ alkyl, or aryl, said alkyl and aryl is optionally substituted with one to three members selected from R$^a$.

3. A compound according to claim 1 wherein X is O.

4. A compound according to claim 1 wherein X is S.

5. A compound according to claim 1 selected from:

2-(2-(3-hydroxy)naphthyl)-4-(3-thiophenyl)-5-acetamidooxazole;

2-(2-(3-hydroxy)naphthyl)-4-(3-thiophenyl)-5-trifluoroacetamido-oxazole;

2-(2-(3-hydroxy)naphthyl)-4-(3-thiophenyl)5-acetamidooxazole;

2-(2-hydroxy-4-phenyl)-phenyl-4-thiophenyl-5-acetarnidooxazole;

2-(2-hydroxy-(4-(3-nitro)-phenyl))-phenyl-4-thiophenyl-5-acetamidooxazole;

2-(2-hydroxy-(4-(1-naphthyl))-phenyl4-thiophenyl-5-acetamidooxazole;

2-(2-hydroxy-(4-(4'-methyl)-phenyl)-phenyl4-thiophenyl-5-acetamidooxazole;

2-(2-hydroxy-(4-(4'-methoxy)-phenyl)-phenyl-4-thiophenyl-5-acetamidooxazole;

2-(2-hydroxy-(4-(3'-chloro)-phenyl)-phenyl-4-thiophenyl-5-acetamidooxazole;

2-(2-hydroxy-(4-(3'-methoxy)-phenyl)-phenyl-4-thiophenyl-5-acetamidooxazole;

2-(2-hydroxy-(4-(3'-fluoro)-phenyl)-phenyl4-thiophenyl-5-acetamidooxazole;

2-(2-hydroxy-(4-(2-naphthyl)-phenyl)-phenyl4-thiophenyl-5-acetamidooxazole;

2-(2-hydroxy-(4-(2-trifluoromethyl)-phenyl)-phenyl-4-thiophenyl-5-acetamidooxazole;

2-(2-hydroxy-4-phenyl)-phenyl4-(3-pyridyl)-5-acetamidooxazole;

2-(2-hydroxy-(4-(3-nitro)-phenyl))-phenyl4-(3-pyridyl)-5-acetamidooxazole;

2-(2-hydroxy-(4-(1-naphthyl))-phenyl4-(3-pyridyl)-5-acetamidooxazole;

2-(2-hydroxy-(4-(4'-methyl)-phenyl)-phenyl4-(3-pyridyl)-5-acetamidooxazole;

2-(2-hydroxy-(4-(4'-methoxy)-phenyl)-phenyl-4-(3-pyridyl)5-acetamidooxazole;

2-(2-hydroxy-(4-(3'-chloro)-phenyl)-phenyl4-(3-pyridyl)-5-acetamidooxazole;

2-(2-hydroxy-(4-(3'-methoxy)-phenyl)-phenyl-4-(3-pyridyl)-5-acetamidooxazole;

2-(2-hydroxy-(4-(3'-fluoro)-phenyl)-phenyl4-(3-pyridyl)-5-acetamidooxazole;

2-(2-hydroxy-(4-(2-naphthyl)-phenyl)-phenyl4-(3-pyridyl)-5-acetamidooxazole;

2-(2-hydroxy-(4-(2-trifluoromethyl)-phenyl)-phenyl4-(3-pyridyl)-5-acetarnidooxazole;

2-(2-hydroxy-4-phenyl)-phenyl4-(3-thiophenyl)-5-acetamidooxazole;

2-(2-hydroxy-(4-(3-nitro)-phenyl))-phenyl4-(3-thiophenyl)-5-acetarnidooxazole;

2-(2-hydroxy-(4-(1-naphthyl))-phenyl4-(3-thiophenyl)-5-acetamidooxazole;

2-(2-hydroxy-(4-(4'-methyl)-phenyl)-phenyl4(3-thiophenyl)-5-acetamidooxazole;

2-(2-hydroxy-(4-(4'-methoxy)-phenyl)-phenyl4(3-thiophenyl)-5-acetamidooxazole;

2-(2-hydroxy-(4-(3'-chloro)-phenyl)-phenyl4(3-thiophenyl)-5-acetarnidooxazole;

2-(2-hydroxy-(4-(3'-methoxy)-phenyl)-phenyl-4-(3-thiophenyl)-5-acetamidooxazole;

2-(2-hydroxy-(4-(3'-fluoro)-phenyl)-phenyl4-(3-thiophenyl)-5-acetamidooxazole;

2-(2-hydroxy-(4-(2-naphthyl)-phenyl)-phenyl4-(3-thiophenyl)-5-acetamidooxazole;

2-(2-hydroxy-(4-(2-trifluoromethyl)-phenyl)-phenyl-4-(3-thiopheny t)-5-acetarnidooxazole;

2-(2-hydroxy-4-phenyl)-phenyl-4-(2-thiophenyl)-5-acetamidooxazole;

2-(2-hydroxy-(4-(3-nitro)-phenyl))-phenyl-4-(2-thiophenyl)-5-acetamidooxazole;

2-(2-hydroxy-(4-(1-naphthyl))-phenyl-4-(2-thiophenyl)-5-acetamidooxazole;

2-(2-hydroxy-(4-(4'-methyl)-phenyl)-phenyl4-(2-thiophenyl)-5-acetamidooxazole;

2-(2-hydroxy-(4-(4-methoxy)-phenyl)-phenyl-4-(2-thiophenyl)-5-acetamidooxazole;

2-(2-hydroxy-(4-(3-chloro)-phenyl)-phenyl-4-(2-thiophenyl)-5-acetamidooxazole;

2-(2-hydroxy-(4-(3'-methoxy)-phenyl)-phenyl-4-(2-thiophenyl)-5-acetarnidooxazole;

2-(2-hydroxy-(4-(3'-fluoro)-phenyl)-phenyl4-(2-thiophenyl)-5-acetamidooxazole;

2-(2-hydroxy-(4-(2-naphthyl)-phenyl)-phenyl4-(2-thiophenyl)-5-acetamidooxazole;

2-(2-hydroxy-(4-(2-trifluoromethyl)-phenyl)-phenyl4-(2-thiophenyl)-5-acetamidooxazole;

2-(2-hydroxy4-phenyl)-phenyl4-thiophenyl-5-benzamidooxazole;

2-(2-hydroxy-(4-(3-nitro)-phenyl))-phenyl4-thiophenyl-5-benzamidooxazole;

2-(2-hydroxy-(4-(1-naphthyl))-phenyl4-thiophenyl-5-benzamidooxazole;

2-(2-hydroxy-(4-(4'-methyl)-phenyl)-phenyl4-thiophenyl-5-benzamidooxazole;

2-(2-hydroxy-(4-(4'-methoxy)-phenyl)-phenyl[]thiophenyl-5-benzamidooxazole;

2-(2-hydroxy-(4-(3'-chloro)-phenyl)-phenyl-4-thiophenyl-5-benzamidooxazole;

2-(2-hydroxy-(4-(3'-methoxy)-phenyl)-phenyl4-thiophenyl-5-benzamidooxazole;

2-(2-hydroxy-(4-(3'-fluoro)-phenyl)-phenyl-4-thiophenyl-5-benzamidooxazole;

2-(2-hydroxy-(4-(2-naphthyl)-phenyl)-phenyl-4-thiophenyl-5-benzamidooxazole;

2-(2-hydroxy-(4-(2-trifluoromethyl)-phenyl)-phenyl[]thiophenyl-5-benzamidooxazole;

2-(2-hydroxy-4-phenyl)-phenyl-4-(3-pyridyl)-5-benzamidooxazole;

2-(2-hydroxy-(4-(3-nitro)-phenyl))-phenyl-4-(3-pyridyl)-5-benzamidooxazole;

2-(2-hydroxy-(4-(1-naphthyl))-phenyl-4-(3-pyridyl)-5-benzamidooxazole;

2-(2-hydroxy-(4-(4'-methyl)-phenyl3-phenyl-4-(3-pyridyl)-5-benzamidooxazole;

2-(2-hydroxy-(4-(4'-methoxy)-phenyl)-phenyl-4-(3-pyridyl)-5-benzamidooxazole;

2-(2-hydroxy-(4-(3 '-chloro)-phenyl)-phenyl-4-(3-pyridyl)-5-benzamidooxazole;

2-(2-hydroxy-(4-(3'-methoxy)-phenyl)-phenyl-4-(3-pyridyl)-5-benzamidooxazole;

2-(2-hydroxy-(4-(3'-fluoro)phenyl)-phenyl-4-(3-pyridyl)-5-benzamidooxazole;

2-(2-hydroxy-(4-(2-naphthyl)-phenyl)-phenyl-4(3-pyridyl)-5-benzamidooxazole;

2-(2-hydroxy-(4-(2-trifluoromethyl)-phenyl)-phenyl4-(3-pyridyl)-5-benzamidooxazole;

2-(2-hydroxy-4-phenyl)-phenyl)4-(4-trifluoromethylphenyl)-5-benzamidooxazole;

2-(2-hydroxy-4-phenyl)-phenyl4-(3-thiophenyl)-5-benzamidooxazole;

2-(2-hydroxy-(3-nitro)-phenyl))-phenyl4-(3-trio phenyl)-5-benzamidooxazole;

2-(2-hydroxy-(4-(1-naphthyl))-phenyl4-(3-thiophenyl)-5-benzamidooxazole;

2-(2-hydroxy-(4-(4'-methyl)-phenyl)-phenyl4-(3-thiophenyl)-5-benzamidooxazole;

2-(2-hydroxy-(4-(4'-methoxy)-phenyl)-phenyl4(3-thiophenyl)-5-benzamidooxazole;

2-(2-hydroxy-(4-(3'-chloro)-phenyl)-phenyl4-(3-thiophenyl)-5-benzamidooxazole;

2-(2-hydroxy-(4-(3'-methoxy)-phenyl)-phenyl-4-(3-thiophenyl)-5-benzamidooxazole;

2-(2-hydroxy-(4-(3'-fluoro)-phenyl)-phenyl4-(3-thiophenyl)-5-benzamidooxazole;

2-(2-hydroxy-(4-(2-naphthyl)-phenyl)-phenyl-4-(3-thiophenyl)-5-benzamidooxazole;

2-(2-hydroxy-(4-(2-trifluoromethyl)-phenyl)-phenyl4-(3-thiopheny t)-5-benzamidooxazole;

2-(2-hydroxy-4-phenyl)-phenyl-4-(2-thiophenyl)-5-benzamidooxazole;

2-(2-hydroxy-(4-(3-nitro)-phenyl3)-phenyl-4-(2-thiophenyl)-5-benzamidooxazole;

2-(2-hydroxy-(4-(1-naphthyl))-phenyl-4-(2-thiophenyl)-5-benzamidooxazole;

2-(2-hydroxy-(4-(4'-methyl)-phenyl)-phenyl-4-(2-thiophenyl)-5-benzamidooxazole;

2-(2-hydroxy-(4-(4'-methoxy)-phenyl)-phenyl4(2-thiophenyl)-5-benzamidooxazole;

2-(2-hydroxy-(4(3-chloro)-phenyl)-phenyl4-(2-thiophenyl)-5-benzamidooxazole;

2-(2-hydroxy-(4-(3'-methoxy)-phenyl)-phenyl-4-(2-thiophenyl)-5-benzamidooxazole;

2-(2-hydroxy-(4-(3-fluoro)-phenyl)-phenyl-4-(2-thiophenyl)-5-benzamidooxazole;

2-(2-hydroxy-(4-(2-naphthyl)-phenyl)-phenyl-4-(2-thiophenyl)-5-benzamidooxazole;

2-(2-hydroxy-(4-(2-trifluoromethyl)-phenyl)phenyl-4(2-thiophenyl)-5-benzamidooxazole;

2-(2-hydroxy-4-phenyl)-phenyl-4-thiophenyl-5-valeramidooxazole;

2-(2-hydroxy-(4-(3-nitro)-phenyl))-phenyl-4thiophenyl-5-valeramidooxazole;

2-(2-hydroxy-(4-(1-naphthyl))-phenyl4-thiophenyl-5-valeramidooxazole;

2-(2-hydroxy-(4-(4'-methyl)-phenyl)-phenyl4-thiophenyl-5-valeramidooxazole;

2-(2-hydroxy-(4-(4'-methoxy)-phenyl)-phenyl4-thiophenyl-5-valeramidooxazole;

2-(2-hydroxy-(4-(3'-chloro)-phenyl)-phenyl-4-thiophenyl-5-valeramidooxazole;

2-(2-hydroxy-(4-(3'-methoxy)-phenyl)-phenyl4-thiophenyl-5-valeramidooxazole;

2-(2-hydroxy-(4-(3'-fluoro)-phenyl)-phenyl-4-thiophenyl-5-valeramidooxazole;

2-(2-hydroxy-(4-(2-napthyl)-phenyl)-phenyl4-thiophenyl-5-valeramdooxazole;

2-(2-hydroxy-(4-(2-trifluoromethyl)-phenyl)-phenyl-4-thiophenyl-5-valeramidooxazole;

2-(2-hydroxy4-phenyl)-phenyl-4-(3-pyridyl)-5-valeramidooxazole;
2-(2-hydroxy-(4-(3-nitro)-phenyl))-phenyl4-(3-pyridyl)-5-valeramidooxazole;
2-(2-hydroxy-(4-(1-naphthyl))-phenyl-4-(3-pyridyl)-5-valeramidooxazole;
2-(2-hydroxy-(4-(4'-methyl)-phenyl)-phenyl-4-(3-pyridyl)-5-valeramidooxazole;
2-(2-hydroxy-(4-(4-methoxy)-phenyl)-phenyl4(3-pyridyl)-5-valeramidooxazole;
2-(2-hydroxy-(4-(3'-chloro)-phenyl)-phenyl-4-(3-pyridyl)-5-valeramidooxazole;
2-(2-hydroxy-(4-(3'-methoxy)-phenyl)-phenyl-4-(3-pyridyl)-5-valeramidooxazole;
2-(2-hydroxy-(4-(3'-fluoro)-phenyl)-phenyl-4-(3-pyridyl)-5-valeramidooxazole;
2-(2-hydroxy-(4-(2-naphthyl)-phenyl)-phenyl4-(3-pyridyl)-5-valeramidooxazole;
2-(2-hydroxy-(4-(2-trifluoromethyl)-phenyl)-phenyl-4-(3-pyridyl)-5-valeramidooxazole;
2-(2-hydroxy-4-phenyl)-phenyl-4-(3-thiophenyl)-5-valeramdooxazole;
2-(2-hydroxy-(4-(3-nitro)-phenyl))-phenyl-4-(3-thiophenyl)-5-valeramidooxazole;
2-(2-hydroxy-(4-(1-naphthyl))-phenyl-4-(3-thiophenyl)-5-valeramidooxazole;
2-(2-hydroxy-(4-(4'-methyl3-phenyl)-phenyl-4-(3-thiophenyl)-5-valeramidooxazole;
2-(2-hydroxy-(4-(4'-methoxy3-phenyl)-phenyl-4-(3-thiophenyl)-5-valeramidooxazole;
2-(2-hydroxy-(4-(3'-chloro) -phenyl)-phenyl-4-(3-thiophenyl)-5-valeramidooxazole;
2-(2-hydroxy-(4-(3'-methoxy)-phenyl)-phenyl -4-(3-thiophenyl)-5-valeramdooxazole;
2-(2-hydroxy-(4-(3'-fluoro)-phenyl)-phenyl -4-(3-thiophenyl) -5-valeramidooxazole;
2-(2-hydroxy-(4-(2-napthyl)-phenyl)-phenyl -4-(3-thiophenyl)-5-valeramdooxazole;
2-(2-hydroxy-(4-(2-trifluoromethyl)-phenyl)-phenyl-4-(3-thiophenyl)-5-valeramidooxazole;
2-(2-hydroxy-4-phenyl)-phenyl -4-(2-thiophenyl)-5-valeramidooxazole;
2-(2-hydroxy-(4-(3-nitro)-phenyl))-phenyl-4-(2-thiophenyl)-5-valeramidooxazole;
2-(2-hydroxy-(4-(1-naphthyl))-phenyl-4-(2-thiophenyl)-5-valeramidooxazole;
2-(2-hydroxy-(4-(4'-methyl)-phenyl)-phenyl-4-(2-thiophenyl)-5-valeramidooxazole;
2-(2-hydroxy-(4-(4'-methoxy)-phenyl)-phenyl-4-(2-thiophenyl)-5-valeramidooxazole;
2-(2-hydroxy-(4-(3'-chloro)-phenyl)-phenyl-4-(2-thiophenyl)-5-valeramidooxazole;
2-(2-hydroxy-(4-(3'-methoxy)-phenyl)-phenyl-4-(2-thiophenyl)-5-valeramdooxazole;
2-(2-hydroxy-(4-(3'-fluoro)-phenyl)-phenyl-4-(2-thiophenyl)-5-valeramdooxazole;
2-(2-hydroxy-(4-(2-naphthyl)-phenyl)-phenyl-4-(2-thiophenyl)-5-valeramdooxazole; and
2-(2-hydroxy-(4-(2-trifluoromethyl)-phenyl)-phenyl -4-(2-thiophenyl)-5-valeramidooxazole;
or a pharmaceutically acceptable salt thereof.

6. A pharmaceutical composition which is comprised of a compound in accordance with claim 1 and a pharmaceutically acceptable carrier.

7. A method of treating cancer in a mammal in need of such treatment which is comprised of administering to said mammal a therapeutically effective amount of a compound of claim 1.

8. A method of treating cancer in accordance with claim 7 wherein the cancer is selected from cancers of the brain, genitourinary tract, lymphatic system, stomach, larynx and lung.

9. A method in accordance with claim 7 wherein the cancer is selected from histiocytic lymphoma, lung adenocarcinoma, small cell lung cancers, pancreatic cancer, gioblastomas and breast carcinoma.

10. A method of treating a disease in which neoangiogenesis is implicated, which is comprised of administering to a mammal in need of such treatment a therapeutically effective amount of a compound of claim 1.

11. A method in accordance with claim 10 wherein the disease is an ocular disease.

12. A method of treating retinal vascularization which is comprised of administering to a mammal in need of such treatment a therapeutically effective amount of compound of claim 1.

13. A method of treating diabetic retinopathy which is comprised of administering to a mammalian need of such treatment a therapeutically effective amount of compound of claim 1.

14. A method of treating age-related macular degeneration which is comprised of administering to a mammal in need of such treatment a therapeutically effective amount of a compound of claim 1.

15. A method of treating inflammatory diseases which comprises administering to a mammal in need of such treatment a therapeutically effective amount of a compound of claim 1.

16. A method according to claim 15 wherein the inflammatory disease is selected from rheumatoid arthritis, psoriasis, contact dermatitis and delayed hypersensitivity reactions.

17. A method for inhibiting tyrosine kinase which comprises administering to a mammal in need of such treatment a therapeutically effective amount of a compound of claim 1.

18. A method of preventing cancer in a mammal in need of such treatment which is comprised of administering to said mammal a therapeutically effective amount of a compound of claim 1.

19. A method of preventing cancer in accordance with claim 18 wherein the cancer is selected from cancers of the brain, genitourinary tract, lymphatic system, stomach, larynx and lung.

20. A method in accordance with claim 19 wherein the cancer is selected from histiocytic lymphoma, lung adenocarcinoma, small cell lung cancers, pancreatic cancer, gioblastomas and breast carcinoma.

21. A method of preventing a disease in which neoangiogenesis is implicated, which is comprised of administering to a mammal in need of such treatment a therapeutically effective amount of a compound of claim 1.

22. A method in accordance with claim 21 wherein the disease is an ocular disease.

23. A method of preventing retinal vascularization which is comprised of administering to a mammal in need of such treatment a therapeutically effective amount of a compound of claim 1.

24. A method of preventing diabetic retinopathy which is comprised of administering to a mammal in need of such treatment a therapeutically effective amount of a compound of claim 1.

25. A method of preventing age-related macular degeneration which is comprised of administering to a mammal in need of such treatment a therapeutically effective amount of a compound of claim 1.

26. A method of preventing inflammatory diseases which is comprised of administering to a mammal in need of such treatment a therapeutically effective amount of a compound of claim 1.

27. A method according to claim 26 wherein the inflammatory disease is selected from rheumatoid arthritis, psoriasis, contact dermatitis and delayed hypersensitivity reactions.

* * * * *

UNITED STATES PATENT AND TRADEMARK OFFICE
CERTIFICATE OF CORRECTION

PATENT NO. : 6,228,871 B1  
DATED : May 8, 2001  
INVENTOR(S) : Mark E. Fraley, Randall W. Hungate, William F. Hoffman, William R. Huckle, Richard L. Kendall and Kenneth A. Thomas, Jr.

Page 1 of 1

It is certified that error appears in the above-identified patent and that said Letters Patent is hereby corrected as shown below:

Column 33, claim 1,  
Line 23, replace R with -- $R^1$ --.  
Line 26, $R_a$ with -- $R^a$ --.

Column 35, claim 5,  
Line 45, replace [] with -- -4- --.  
Line 53, should read as follows -- 2-(2-hydroxy-(4-(4'-methyl)-phenyl-4-(3- --.

Column 36, claim 5,  
Line 5, should read follows -- 2-(2-hydroxy-(4-(3-nitro)-phenyl))-phenyl-4-(3-thiophenyl)- --.  
Line 24, should read as follows -- thiophenyl)-5-benzamidooxazole; --.

Column 37, claim 5,  
Line 29, should read as follows -- 2-(2-hydroxy-(4-(4'-methyl)-phenyl-4-(3- --.  
Line 31, should read as follows -- 2-(2-hydroxy-(4-(4'-methoxy)-phenyl)-phenyl-4-(3- --.

Signed and Sealed this

Nineteenth Day of February, 2002

Attest:

Attesting Officer

JAMES E. ROGAN  
Director of the United States Patent and Trademark Office